(12) United States Patent
Sgroi, Jr. et al.

(10) Patent No.: US 11,350,939 B2
(45) Date of Patent: Jun. 7, 2022

(54) RETAINING MECHANISMS FOR TROCAR ASSEMBLIES

(71) Applicant: Covidien LP, Mansfield, MA (US)

(72) Inventors: Anthony Sgroi, Jr., Wallingford, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 260 days.

(21) Appl. No.: 16/827,900

(22) Filed: Mar. 24, 2020

(65) Prior Publication Data

US 2021/0298754 A1    Sep. 30, 2021

(51) Int. Cl.
  *A61B 17/34*     (2006.01)
  *A61B 17/115*    (2006.01)
  *A61B 17/00*     (2006.01)

(52) U.S. Cl.
  CPC ...... *A61B 17/1155* (2013.01); *A61B 17/3462* (2013.01); *A61B 2017/0046* (2013.01)

(58) Field of Classification Search
  CPC ............ A61B 17/1155; A61B 17/3462; A61B 2017/0046; A61B 17/068; A61B 17/10; A61B 17/32053; A61B 17/34; A61B 2017/07257; A61B 2017/07285; A61B 2017/00473; A61B 2017/00477
  USPC ...................... 227/175.1–182.1; 606/75, 219
  See application file for complete search history.

(56) References Cited

U.S. PATENT DOCUMENTS

| | | | |
|---|---|---|---|
| 3,193,165 A | 7/1965 | Akhalaya et al. | |
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Aug. 16, 2021, corresponding to counterpart European Application No. 21164195.6; 12 pages.

*Primary Examiner* — Robert F Long
(74) *Attorney, Agent, or Firm* — Carter, DeLuca & Farrell LLP

(57) ABSTRACT

Adapter assemblies for connecting loading units to handle assemblies include a trocar assembly releasably securable within an elongate body by a retaining mechanism. The retaining mechanism includes first and second retention members pivotable between a locked position in which the first and second retention members are positioned to be received within respective first and second openings in a trocar housing of the trocar assembly when the trocar assembly is received within a distal portion of the elongate body, and a release position in which the first and second retention members are positioned to be spaced from the respective first and second openings in the trocar housing when the trocar assembly is received within the distal portion of the elongate body, wherein engagement of the first and second retention members with the seal member when in the locked position frictionally retains the first and second retention members in the locked position.

19 Claims, 33 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,071,430 A * | 12/1991 | de Salis ............ A61B 17/07207 606/219 |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Mien et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | | |
|---|---|---|---|
| 6,387,105 | B1 | 5/2002 | Gifford, III et al. |
| 6,398,795 | B1 | 6/2002 | McAlister et al. |
| 6,402,008 | B1 | 6/2002 | Lucas |
| 6,439,446 | B1 | 8/2002 | Perry et al. |
| 6,443,973 | B1 | 9/2002 | Whitman |
| 6,450,390 | B2 | 9/2002 | Heck et al. |
| 6,478,210 | B2 | 11/2002 | Adams et al. |
| 6,488,197 | B1 | 12/2002 | Whitman |
| 6,491,201 | B1 | 12/2002 | Whitman |
| 6,494,877 | B2 | 12/2002 | Odell et al. |
| 6,503,259 | B2 | 1/2003 | Huxel et al. |
| 6,517,566 | B1 | 2/2003 | Hovland et al. |
| 6,520,398 | B2 | 2/2003 | Nicolo |
| 6,533,157 | B1 | 3/2003 | Whitman |
| 6,551,334 | B2 | 4/2003 | Blatter et al. |
| 6,578,751 | B2 | 6/2003 | Hartwick |
| 6,585,144 | B2 | 7/2003 | Adams et al. |
| 6,588,643 | B2 | 7/2003 | Bolduc et al. |
| 6,592,596 | B1 | 7/2003 | Geitz |
| 6,601,749 | B2 | 8/2003 | Sullivan et al. |
| 6,605,078 | B2 | 8/2003 | Adams |
| 6,605,098 | B2 | 8/2003 | Nobis et al. |
| 6,626,921 | B2 | 9/2003 | Blatter et al. |
| 6,629,630 | B2 | 10/2003 | Adams |
| 6,631,837 | B1 | 10/2003 | Heck |
| 6,632,227 | B2 | 10/2003 | Adams |
| 6,632,237 | B2 | 10/2003 | Ben-David et al. |
| 6,652,542 | B2 | 11/2003 | Blatter et al. |
| 6,659,327 | B2 | 12/2003 | Heck et al. |
| 6,676,671 | B2 | 1/2004 | Robertson et al. |
| 6,681,979 | B2 | 1/2004 | Whitman |
| 6,685,079 | B2 | 2/2004 | Sharma et al. |
| 6,695,198 | B2 | 2/2004 | Adams et al. |
| 6,695,199 | B2 | 2/2004 | Whitman |
| 6,698,643 | B2 | 3/2004 | Whitman |
| 6,716,222 | B2 | 4/2004 | McAlister et al. |
| 6,716,233 | B1 | 4/2004 | Whitman |
| 6,726,697 | B2 | 4/2004 | Nicholas et al. |
| 6,742,692 | B2 | 6/2004 | Hartwick |
| 6,743,244 | B2 | 6/2004 | Blatter et al. |
| 6,763,993 | B2 | 7/2004 | Bolduc et al. |
| 6,769,590 | B2 | 8/2004 | Vresh et al. |
| 6,769,594 | B2 | 8/2004 | Orban, III |
| 6,820,791 | B2 | 11/2004 | Adams |
| 6,821,282 | B2 | 11/2004 | Perry et al. |
| 6,827,246 | B2 | 12/2004 | Sullivan et al. |
| 6,840,423 | B2 | 1/2005 | Adams et al. |
| 6,843,403 | B2 | 1/2005 | Whitman |
| 6,846,308 | B2 | 1/2005 | Whitman et al. |
| 6,852,122 | B2 | 2/2005 | Rush |
| 6,866,178 | B2 | 3/2005 | Adams et al. |
| 6,872,214 | B2 | 3/2005 | Sonnenschein et al. |
| 6,874,669 | B2 | 4/2005 | Adams et al. |
| 6,884,250 | B2 | 4/2005 | Monassevitch et al. |
| 6,905,504 | B1 | 6/2005 | Vargas |
| 6,938,814 | B2 | 9/2005 | Sharma et al. |
| 6,942,675 | B1 | 9/2005 | Vargas |
| 6,945,444 | B2 | 9/2005 | Gresham et al. |
| 6,953,138 | B1 | 10/2005 | Dworak et al. |
| 6,957,758 | B2 | 10/2005 | Aranyi |
| 6,959,851 | B2 | 11/2005 | Heinrich |
| 6,978,922 | B2 | 12/2005 | Bilotti et al. |
| 6,981,941 | B2 | 1/2006 | Whitman et al. |
| 6,981,979 | B2 | 1/2006 | Nicolo |
| 7,032,798 | B2 | 4/2006 | Whitman et al. |
| 7,059,331 | B2 | 6/2006 | Adams et al. |
| 7,059,510 | B2 | 6/2006 | Orban, III |
| 7,077,856 | B2 | 7/2006 | Whitman |
| 7,080,769 | B2 | 7/2006 | Vresh et al. |
| 7,086,267 | B2 | 8/2006 | Dworak et al. |
| 7,114,642 | B2 | 10/2006 | Whitman |
| 7,118,528 | B1 | 10/2006 | Piskun |
| 7,122,044 | B2 | 10/2006 | Bolduc et al. |
| 7,128,748 | B2 | 10/2006 | Mooradian et al. |
| 7,141,055 | B2 | 11/2006 | Abrams et al. |
| 7,168,604 | B2 | 1/2007 | Milliman et al. |
| 7,179,267 | B2 | 2/2007 | Nolan et al. |
| 7,182,239 | B1 | 2/2007 | Myers |
| 7,195,142 | B2 | 3/2007 | Orban, III |
| 7,207,168 | B2 | 4/2007 | Doepker et al. |
| 7,220,237 | B2 | 5/2007 | Gannoe et al. |
| 7,234,624 | B2 | 6/2007 | Gresham et al. |
| 7,235,089 | B1 | 6/2007 | McGuckin, Jr. |
| RE39,841 | E | 9/2007 | Bilotti et al. |
| 7,285,125 | B2 | 10/2007 | Viola |
| 7,303,106 | B2 | 12/2007 | Milliman et al. |
| 7,303,107 | B2 | 12/2007 | Milliman et al. |
| 7,309,341 | B2 | 12/2007 | Ortiz et al. |
| 7,322,994 | B2 | 1/2008 | Nicholas et al. |
| 7,325,713 | B2 | 2/2008 | Aranyi |
| 7,334,718 | B2 | 2/2008 | McAlister et al. |
| 7,335,212 | B2 | 2/2008 | Edoga et al. |
| 7,364,060 | B2 | 4/2008 | Milliman |
| 7,398,908 | B2 | 7/2008 | Holsten et al. |
| 7,399,305 | B2 | 7/2008 | Csiky et al. |
| 7,401,721 | B2 | 7/2008 | Holsten et al. |
| 7,401,722 | B2 | 7/2008 | Hur |
| 7,407,075 | B2 | 8/2008 | Holsten et al. |
| 7,410,086 | B2 | 8/2008 | Ortiz et al. |
| 7,422,137 | B2 | 9/2008 | Manzo |
| 7,422,138 | B2 | 9/2008 | Bilotti et al. |
| 7,431,191 | B2 | 10/2008 | Milliman |
| 7,438,718 | B2 | 10/2008 | Milliman et al. |
| 7,455,676 | B2 | 11/2008 | Holsten et al. |
| 7,455,682 | B2 | 11/2008 | Viola |
| 7,481,347 | B2 | 1/2009 | Roy |
| 7,494,038 | B2 | 2/2009 | Milliman |
| 7,506,791 | B2 | 3/2009 | Omaits et al. |
| 7,516,877 | B2 | 4/2009 | Aranyi |
| 7,527,185 | B2 | 5/2009 | Harari et al. |
| 7,537,602 | B2 | 5/2009 | Whitman |
| 7,540,839 | B2 | 6/2009 | Butler et al. |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,556,186 | B2 | 7/2009 | Milliman |
| 7,559,451 | B2 | 7/2009 | Sharma et al. |
| 7,585,306 | B2 | 9/2009 | Abbott et al. |
| 7,588,174 | B2 | 9/2009 | Holsten et al. |
| 7,600,663 | B2 | 10/2009 | Green |
| 7,611,038 | B2 | 11/2009 | Racenet et al. |
| 7,635,385 | B2 | 12/2009 | Milliman et al. |
| 7,669,747 | B2 | 3/2010 | Weisenburgh, II et al. |
| 7,686,201 | B2 | 3/2010 | Csiky |
| 7,694,864 | B2 | 4/2010 | Okada et al. |
| 7,699,204 | B2 | 4/2010 | Viola |
| 7,708,181 | B2 | 5/2010 | Cole et al. |
| 7,717,313 | B2 | 5/2010 | Criscuolo et al. |
| 7,721,932 | B2 | 5/2010 | Cole et al. |
| 7,726,539 | B2 | 6/2010 | Holsten et al. |
| 7,743,958 | B2 | 6/2010 | Orban, III |
| 7,744,627 | B2 | 6/2010 | Orban, III et al. |
| 7,770,776 | B2 | 8/2010 | Chen et al. |
| 7,771,440 | B2 | 8/2010 | Ortiz et al. |
| 7,776,060 | B2 | 8/2010 | Mooradian et al. |
| 7,793,813 | B2 | 9/2010 | Bettuchi |
| 7,802,712 | B2 | 9/2010 | Milliman et al. |
| 7,823,592 | B2 | 11/2010 | Bettuchi et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,845,536 | B2 | 12/2010 | Viola et al. |
| 7,845,538 | B2 | 12/2010 | Whitman |
| 7,857,187 | B2 | 12/2010 | Milliman |
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |

(56) References Cited

U.S. PATENT DOCUMENTS

| | | |
|---|---|---|
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,978,954 B2 * | 3/2015 | Shelton, IV ....... A61B 17/0643 227/175.1 |
| 9,433,416 B2 * | 9/2016 | Beardsley ............ A61B 17/068 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0290855 A1 * | 12/2011 | Moore ............ A61B 17/07207 227/180.1 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |

(56) References Cited

U.S. PATENT DOCUMENTS

| | | |
|---|---|---|
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0158741 A1* | 6/2014 | Woodard, Jr. ...... A61B 17/0401 227/175.1 |
| 2014/0352463 A1* | 12/2014 | Parihar ............ A61B 17/07207 74/25 |
| 2015/0014392 A1* | 1/2015 | Williams ............ A61B 17/072 227/180.1 |
| 2016/0106406 A1* | 4/2016 | Cabrera ............ A61B 17/1155 606/1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0296234 A1* | 10/2016 | Richard ............ A61B 17/1155 |
| 2016/0302792 A1 | 10/2016 | Motai |
| 2016/0361057 A1* | 12/2016 | Williams ............ A61B 17/068 |
| 2016/0374667 A1* | 12/2016 | Miller ................ A61B 17/068 227/175.2 |
| 2017/0086879 A1* | 3/2017 | Williams ............ A61B 17/3417 |
| 2017/0196566 A1* | 7/2017 | Sgroi ................. A61B 17/1155 |
| 2017/0224345 A1* | 8/2017 | Cabrera ............ A61B 17/3476 |
| 2017/0340348 A1* | 11/2017 | Cabrera ............ A61B 17/1155 |
| 2017/0340351 A1* | 11/2017 | Sgroi, Jr. ........... A61B 17/3417 |
| 2019/0090873 A1* | 3/2019 | Fox .................... A61B 17/1155 |
| 2020/0222050 A1* | 7/2020 | Eisinger ............ A61B 17/1155 |
| 2020/0405304 A1* | 12/2020 | Mozdzierz .......... A61B 17/072 |
| 2021/0000472 A1* | 1/2021 | Sgroi, Jr. ........... A61B 17/1155 |
| 2021/0000473 A1* | 1/2021 | Sgroi, Jr. ............ A61B 17/068 |
| 2021/0000500 A1* | 1/2021 | Sgroi, Jr. ........... A61B 17/1155 |
| 2021/0298755 A1* | 9/2021 | Sgroi ................. A61B 17/1155 |
| 2021/0298756 A1* | 9/2021 | Eisinger ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3103402 A1 | 12/2016 |
| EP | 3146905 A1 | 3/2017 |
| EP | 3165180 A2 | 5/2017 |
| EP | 3192462 A1 | 7/2017 |
| EP | 3205290 A2 | 8/2017 |
| EP | 3245959 A2 | 11/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

\* cited by examiner

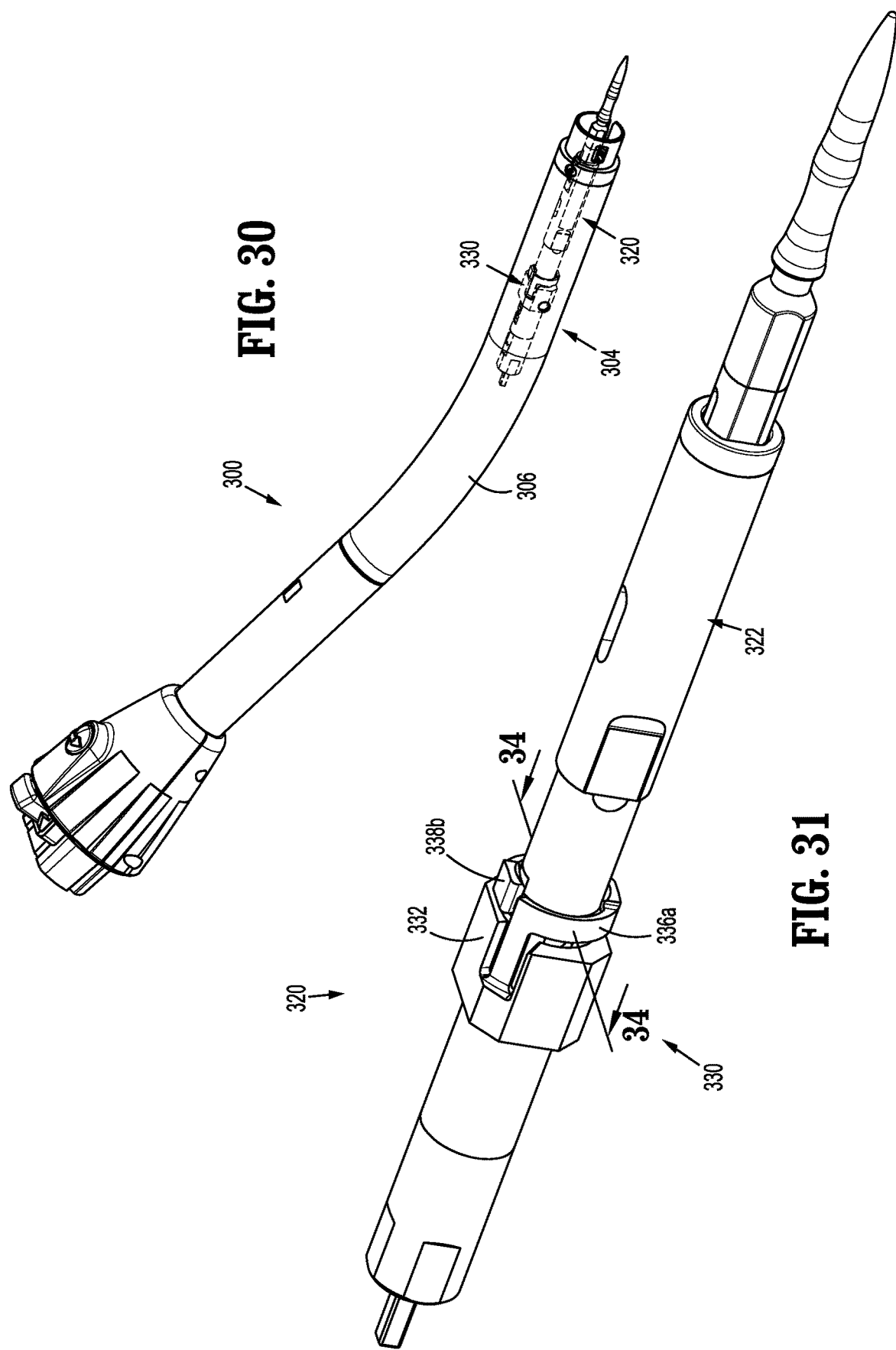

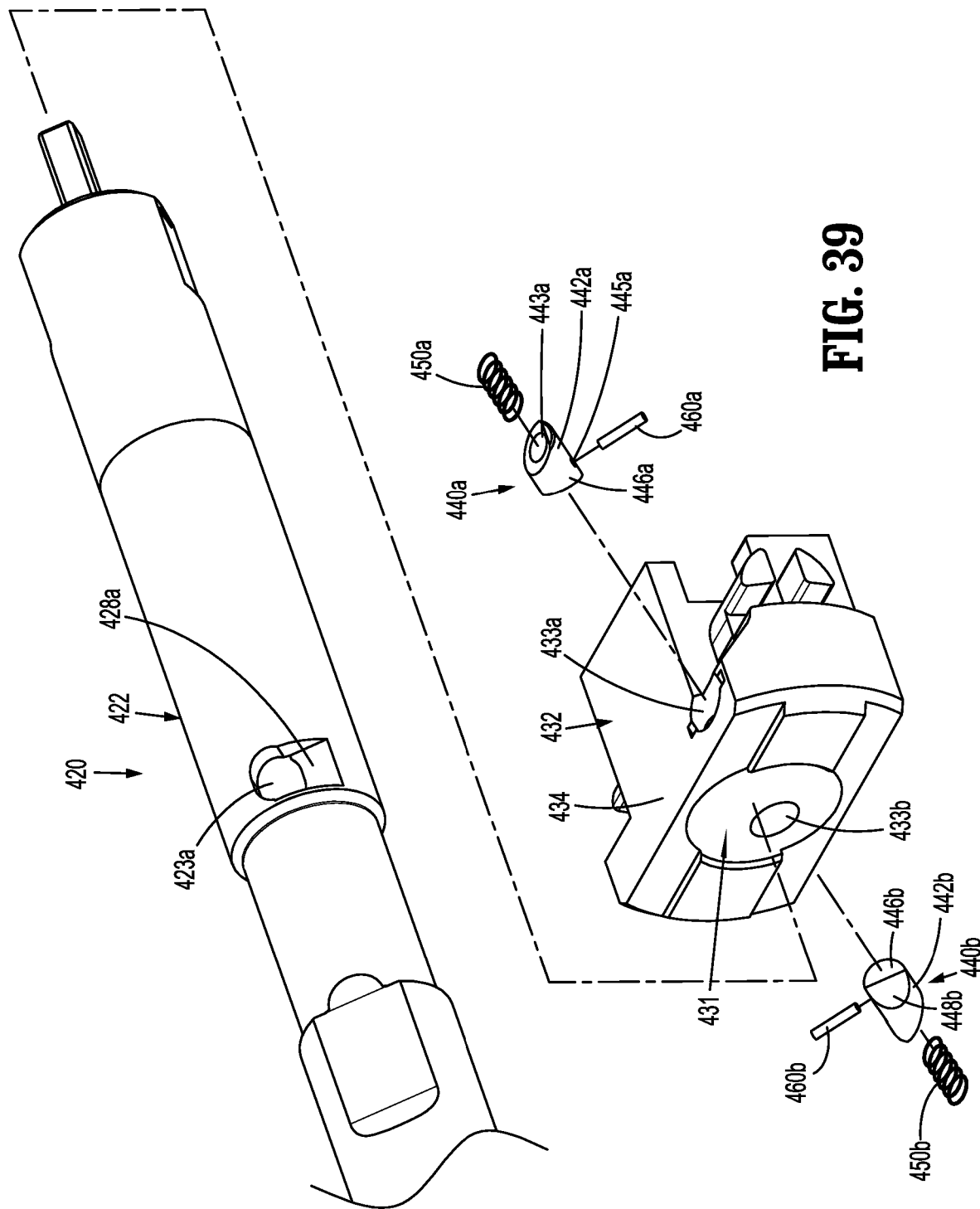

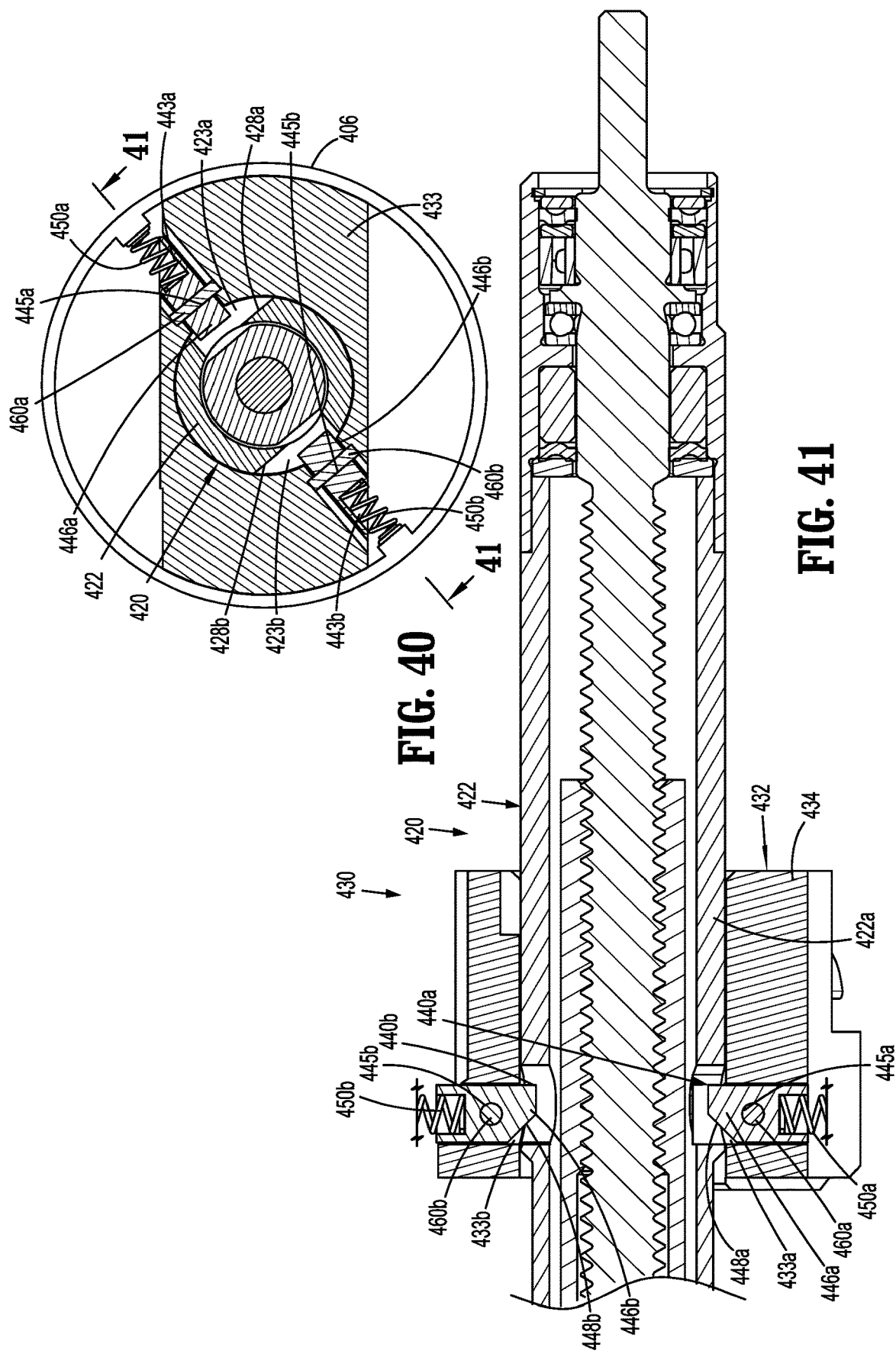

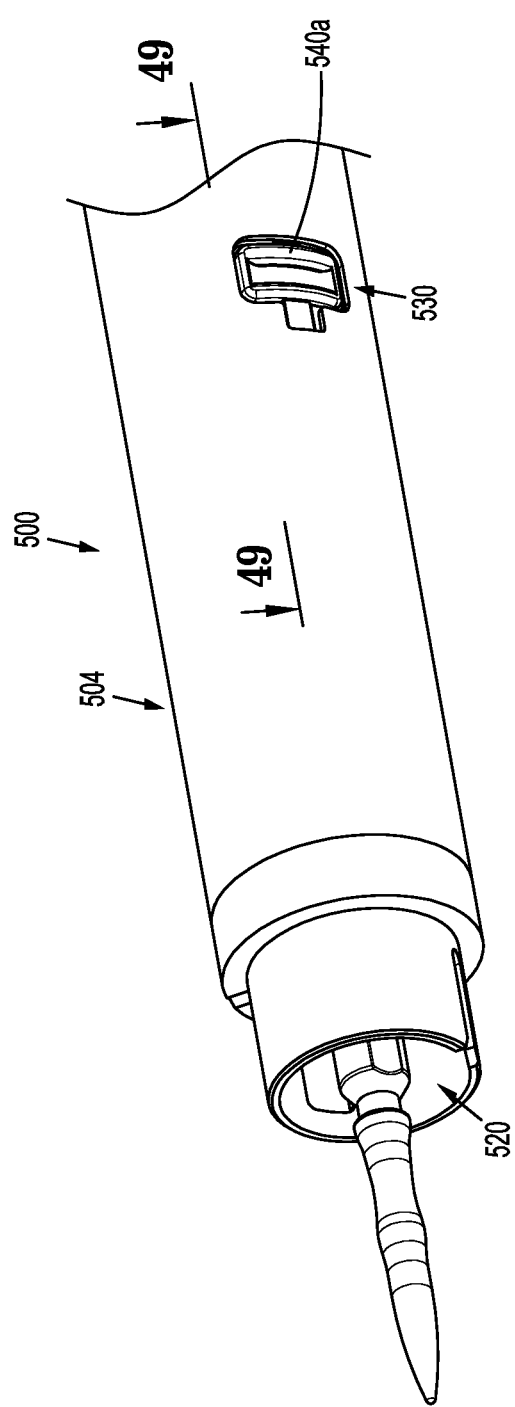
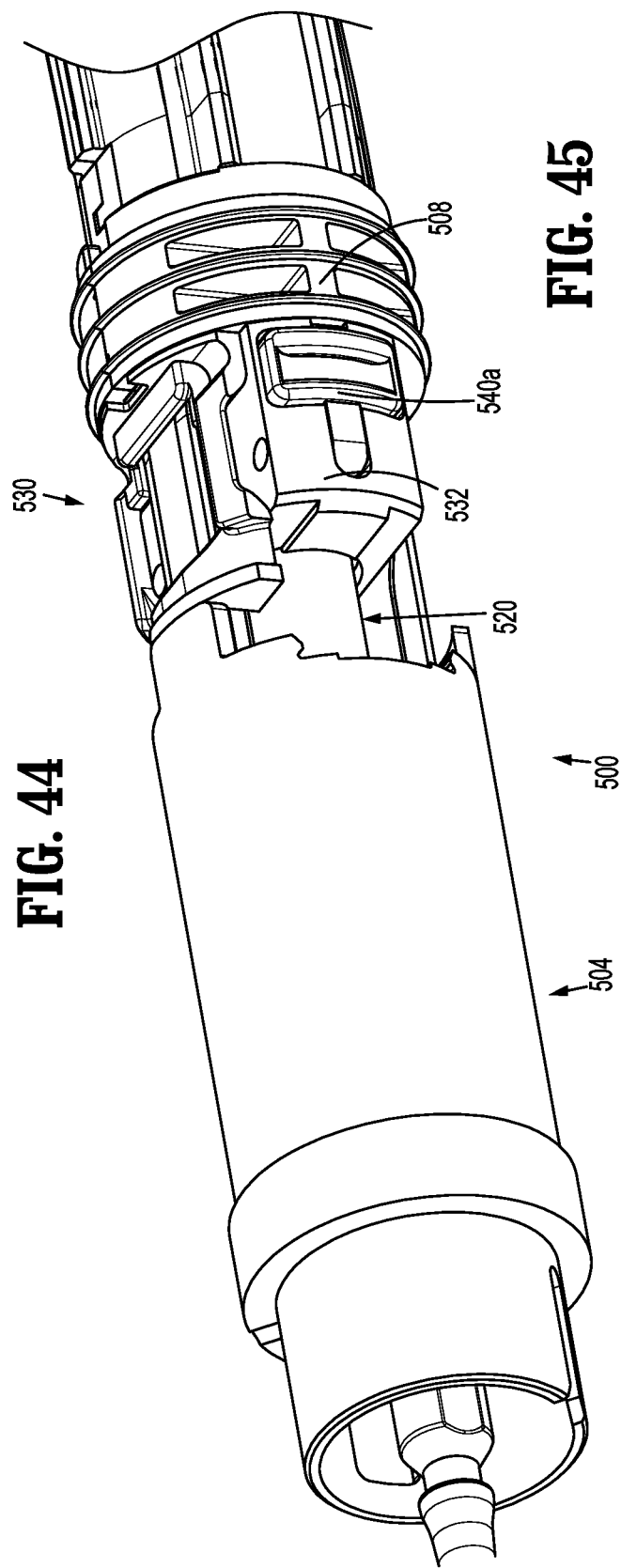

RETAINING MECHANISMS FOR TROCAR ASSEMBLIES

FIELD

The disclosure relates to reusable adapter assemblies for surgical stapling devices. More particularly, the disclosure relates to a retaining mechanism for releasably securing a removable trocar assembly within a reusable adapter assembly.

BACKGROUND

Surgical devices for applying staples, clips, or other fasteners to tissue are well known. Typically, endoscopic stapling devices include an actuation unit, e.g., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly.

Circular stapling devices typically include a trocar assembly for supporting an attached anvil assembly. The trocar assembly may be releasably securable within the adapter assembly to permit cleaning, sterilization, and reuse of the adapter assembly. It would be beneficial to have a retaining mechanism for releasably securing the trocar assembly with the adapter assembly.

SUMMARY

Adapter assemblies for connecting loading units to handle assemblies include an elongate body, a trocar assembly releasably securable with the elongate body, and a retaining mechanism configured to releasably secure the trocar assembly within the sleeve and to facilitate cleaning and sterilizing of the adapter assembly.

An adapter assembly for connecting a loading unit to a handle assembly includes an elongate body having a proximal portion and a distal portion, the proximal portion being configured for operably engagement with an actuation assembly and the distal portion defining a longitudinal axis and being configured to operably receive a trocar assembly. The adapter assembly further includes a seal member disposed within the distal portion of the elongate body, and a retaining mechanism disposed adjacent the seal member and configured to releasably secure the trocar assembly within the distal portion of the elongate body. The retaining mechanism includes first and second retention members. The first and second retention members are pivotable between a locked position in which the first and second retention members are positioned to be received within respective first and second openings in a trocar housing of the trocar assembly when the trocar assembly is received within the distal portion of the elongate body, and a release position in which the first and second retention members are positioned to be spaced from the respective first and second openings in the trocar housing when the trocar assembly is received within the distal portion of the elongate body, wherein engagement of the first and second retention members with the seal member when in the locked position frictionally retains the first and second retention members in the locked position.

In some aspects of the disclosure, the seal member is formed of an elastomeric material. The retaining mechanism may include a housing. The first and second retention members may be pivotally secured to the housing. The housing may define a longitudinal passage for receipt of the trocar assembly. The housing may define first and second recesses for receiving the respective first and second retention members. Each of the first and second retention members may include a camming surface configured to engage the trocar housing during receipt of the trocar assembly within the distal portion of the elongate body. Each of the first and second retention members may include a locking surface configured to engage the trocar housing when the first and second retention members are in the locked position. Each of the first and second retention members may include an engagement surface configured to frictionally engage the seal member to maintain the first and second retention members in the locked position. Each of the first and second retention members may define a slot configured to facilitate engagement of the first and second retention members by a user. The adapter assembly may further include a trocar assembly releasably securable within the distal portion of the elongate body, the trocar assembly including a trocar housing defining first and second openings.

A surgical stapling device includes an actuation assembly, and an adapter assembly including an elongate body having a proximal portion and a distal portion, the proximal portion in operable engagement with the actuation assembly. The surgical stapling device further includes a trocar assembly releasably securable within the distal portion of the adapter assembly, a seal member disposed within the distal portion of the elongate body, and a retaining mechanism disposed adjacent the seal member and configured to releasably secure the trocar assembly within the distal portion of the elongate body. The trocar assembly includes a trocar housing defining first and second openings. The retaining mechanism includes first and second retention members. The first and second retention members are pivotable between a locked position in which the first and second retention members are positioned to be received within respective first and second openings in a trocar housing of the trocar assembly when the trocar assembly is received within the distal portion of the elongate body, and a release position in which the first and second retention members are positioned to be spaced from the respective first and second openings in the trocar housing when the trocar assembly is received within the distal portion of the elongate body. Engagement of the first and second retention members with the seal member when in the locked position frictionally retains the first and second retention members in the locked position.

In some aspects of the disclosure, the seal member is formed of an elastomeric material. The retaining mechanism may include a housing. The first and second retention members may be pivotally secured to the housing. The housing may define a longitudinal passage for receipt of the trocar assembly. The housing may define first and second recesses for receiving the respective first and second retention members. Each of the first and second retention members may include a camming surface configured to engage the trocar housing during receipt of the trocar assembly within the distal portion of the elongate body. Each of the first and second retention members may include a locking surface configured to engage the trocar housing when the first and second retention members are in the locked position. Each of the first and second retention members may include an engagement surface configured to frictionally engage the seal member to maintain the first and second retention members in the locked position. Each of the first and second retention members may define a slot configured to facilitate engagement of the first and second retention members by a user.

In an exemplary aspect of the disclosure, the retaining mechanism includes first and second retention members. The first and second retention members are movable between a locked position in which the first and second retention members are received within the respective first and second openings in the trocar housing and a release position in which the first and second retention members are spaced from the respective first and second retention members. Each of the first and second retention members includes a first camming surface configured to engage a proximal end of the trocar housing as the trocar assembly is received within the outer sleeve to move the first and second retention members to the release position, and a second camming surface configured to engage the trocar housing when the trocar assembly is rotated about a longitudinal axis within the outer sleeve to move the first and second retention members to the release position.

In another exemplary aspect of the disclosure, the retaining mechanism includes a housing and an insert member. The housing defines a longitudinal opening for receipt of the trocar assembly and a slot in communication with the longitudinal opening for receipt of the insert member. The insert member defines an opening for receipt of the trocar assembly and including first, second, and third flat sections, corresponding to the first, second, and third flat sections of the trocar housing, wherein the first, second, and third flat sections of the trocar housing align with the first, second, and third flat sections of the insert member when the trocar assembly is in a first rotational orientation, and the first, second, and third flat sections of the trocar housing are misaligned with the first, second, and third flat sections of the insert member when the trocar assembly is in a second rotational orientation.

In yet another exemplary aspect of the disclosure, the retaining mechanism includes a housing, and first and second flexible arms extending from the housing. The first and second flexible arms each including a free end and a locking portion disposed on the free end. The locking portions of the first and second flexible arms are receivable within the first and second cutouts. The trocar assembly is rotatable within the outer sleeve from a first rotational orientation in which the locking portions of the first and second arms are received within the respective first and second cutouts to a second rotational orientation in which the locking portions of the first and second arms are spaced from the respective first and second cutouts.

In still another exemplary aspect of the disclosure, the retaining mechanism includes first and second retention members. The first and second retention members are movable between a locked position in which the first and second retention members are received within respective first and second cutouts in the trocar housing and a release position in which the first and second retention members are spaced from the respective first and second retention members. Each of the first and second retention members includes a first camming surface configured to engage a proximal end of the trocar housing as the trocar assembly is received within the outer sleeve to move the first and second retention members to the release position. The first and second cam surfaces of the trocar housing engage the respective first and second retention members as the trocar assembly is rotated within the outer sleeve about the longitudinal axis to move the first and second retention members to the release position.

In still yet another exemplary aspect of the disclosure, the retaining mechanism includes first and second retention members. The first and second retention members are pivotable between a locked position in which the first and second retention members are received within the respective first and second openings in the trocar housing and a release position in which the first and second retention members are spaced from the respective first and second openings in the trocar housing. Engagement of the first and second retention members with the seal member when in the locked position frictionally retains the first and second retention members in the locked position.

In another exemplary aspect of the disclosure, the retaining mechanism includes a cam wire moveable between first and second positions, a button member for moving the cam wire between the first and second positions, and first and second retention members movable between a locked position when the cam wire is in the first position and a release position when the cam wire is in the second position. The button member includes a flange engageable with the stop feature of the drive member when the drive member is in the first longitudinal position and the flange is spaced from the stop feature when the drive member is in the second longitudinal position.

In still another exemplary aspect of the disclosure, the retaining mechanism includes first and second retention members. The first and second retention members are pivotable between a locked position in which the first and second retention members are received within the respective first and second openings in the trocar housing and a release position in which the first and second retention members are spaced from the respective first and second openings. Engagement of the first and second retention members with the seal member when in the locked position frictionally retains the first and second retention members in the locked position. Longitudinal movement of the trocar assembly in a first longitudinal direction when the first and second retention members are in the locked position moves the first and second retention members to the release position.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 30 is a perspective view of an adapter assembly according to still another exemplary embodiment of the disclosure including a trocar assembly secured within the adapter assembly by a retaining mechanism;

FIG. 31 is an enlarged perspective view of the trocar assembly and the retaining mechanism shown in FIG. 30;

FIG. 39 is a side perspective view of a proximal end of the trocar assembly and the retaining mechanism shown in FIG. 38, with components of the retaining mechanism separated;

FIG. 40 is a cross-sectional end view of the trocar assembly and the retaining mechanism shown in FIGS. 38 and 39, taken along section line 40-40 shown in FIG. 38, with the retaining mechanism in a locked condition;

FIG. 41 is a cross-sectional view of the trocar assembly and the retaining mechanism shown in FIGS. 38-40, taken along section line 41-41 shown in FIG. 40, with the trocar assembly fully received through the retaining mechanism;

FIG. 44 is a side perspective view of a distal end of an adapter assembly according still yet another exemplary embodiment of the disclosure;

FIG. 45 is an enlarged view of the distal end of the adapter assembly shown in FIG. 44, with an outer sleeve removed and including a trocar assembly and a retaining mechanism;

DETAILED DESCRIPTION

Figure 1:
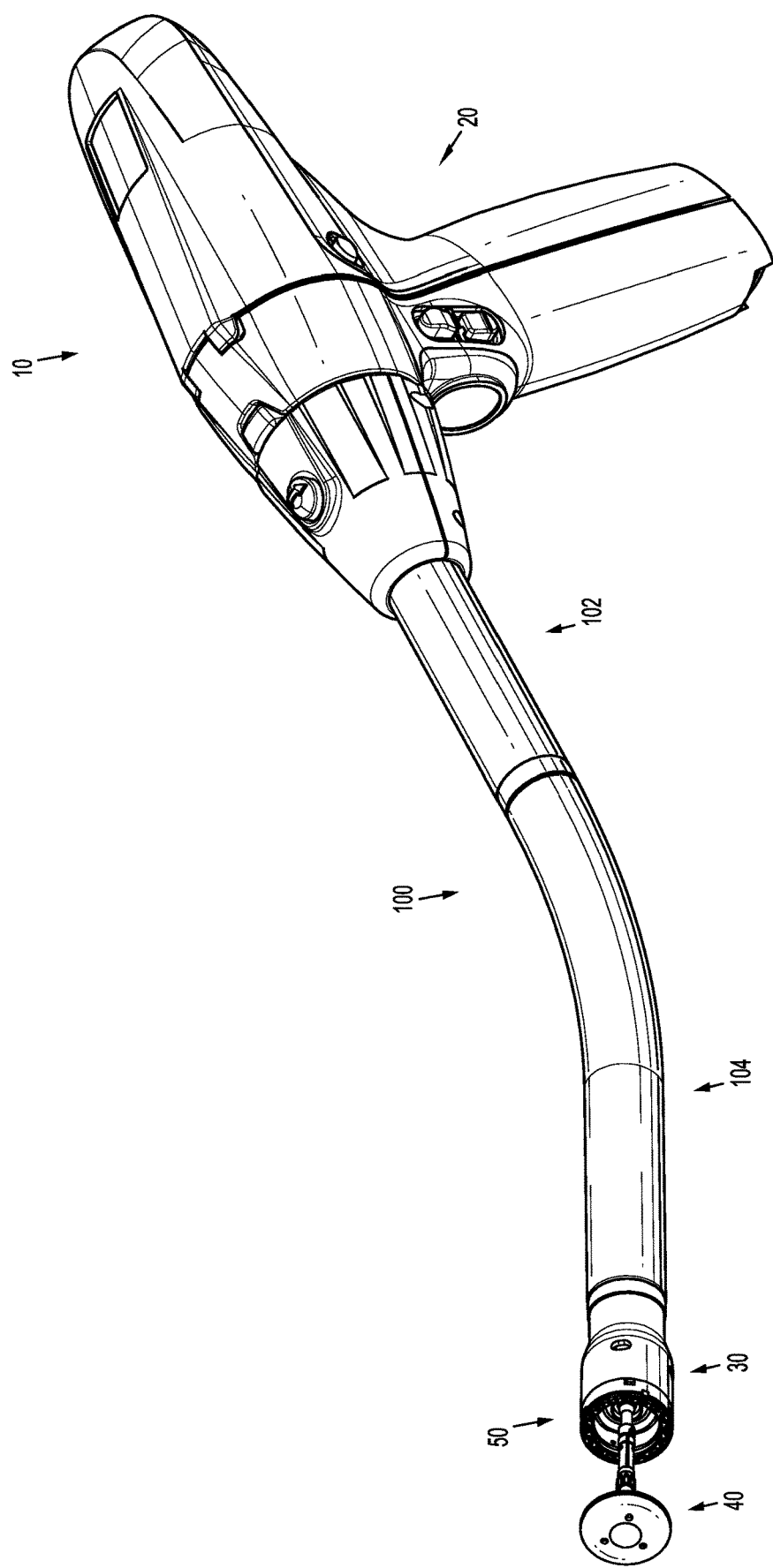
FIG. 1 is a perspective view of a surgical stapling device including a handle assembly and an adapter assembly according to an exemplary embodiment of the disclosure.

Embodiments of the disclosed adapter assembly including a retaining mechanism for securing a removable trocar assembly therein will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

FIG. 1 illustrates a surgical stapling device 10 including an adapter assembly according to an exemplary embodiment of the disclosure, shown generally as adapter assembly 100. The surgical stapling device 10 further includes a powered handle assembly 20, a loading unit 30, and an anvil assembly 40. The loading unit 30 and anvil assembly 40 together form an end effector 50. Although shown and described with reference to surgical stapling device 10, aspects of the disclosure may be modified for use with manual surgical stapling devices having various configurations, and with powered surgical stapling devices having alternative configurations. For a detailed description of exemplary surgical stapling devices, please refer to U.S. Pat. No. 9,023,014 and U.S. Pat. Appl. Publ. No. 2012/0253329.

Figure 2:
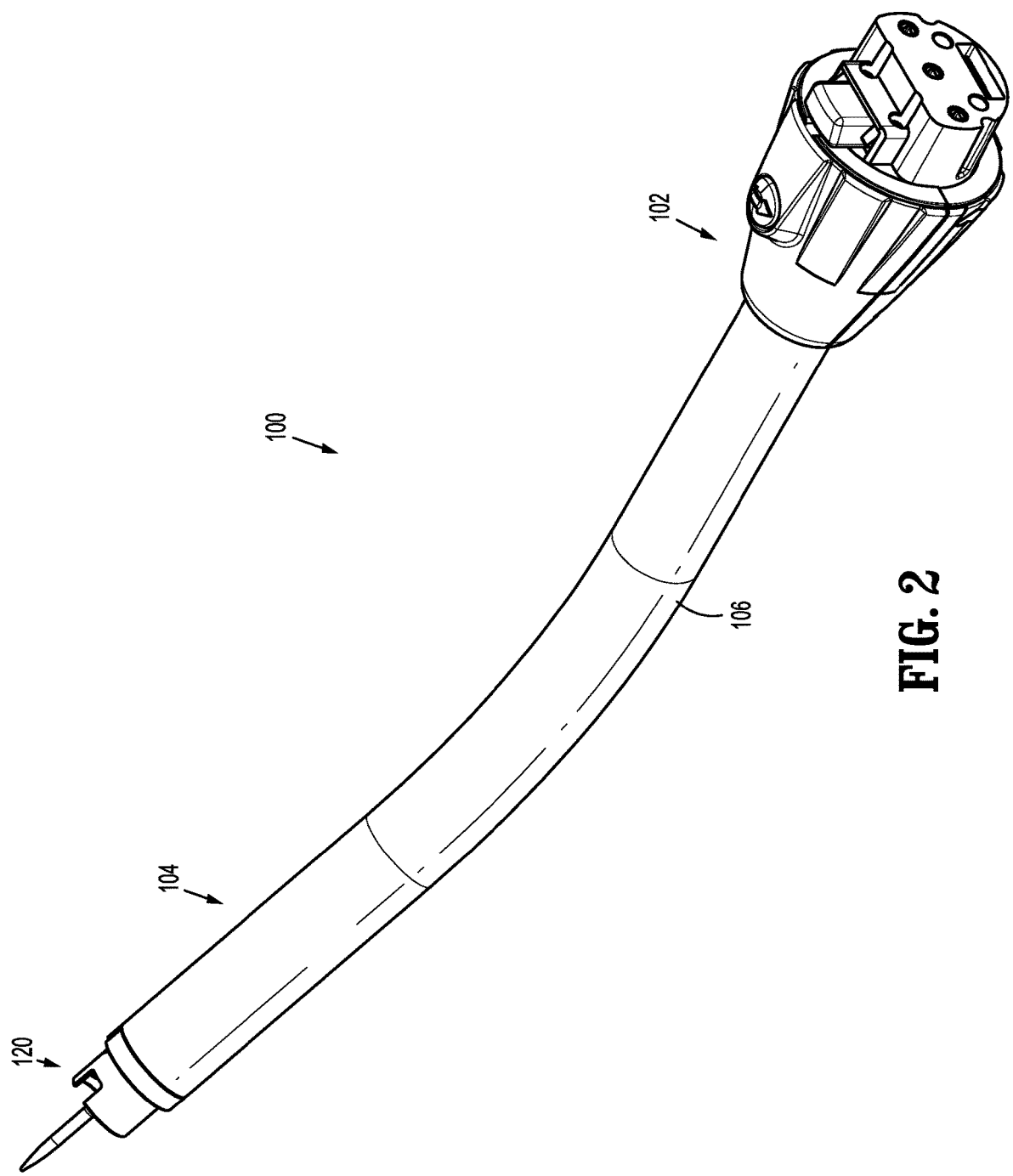
FIG. 2 is a perspective view of the adapter assembly shown in FIG. 1 with a trocar assembly extending from a distal portion of the adapter assembly.

FIG. 2 illustrates the adapter assembly 100 including an elongate body having a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the disclosure. For a detailed description of an exemplary adapter assembly, please refer to U.S. Pat. No. 10,226,254 ("the '254 patent).

Figure 3:
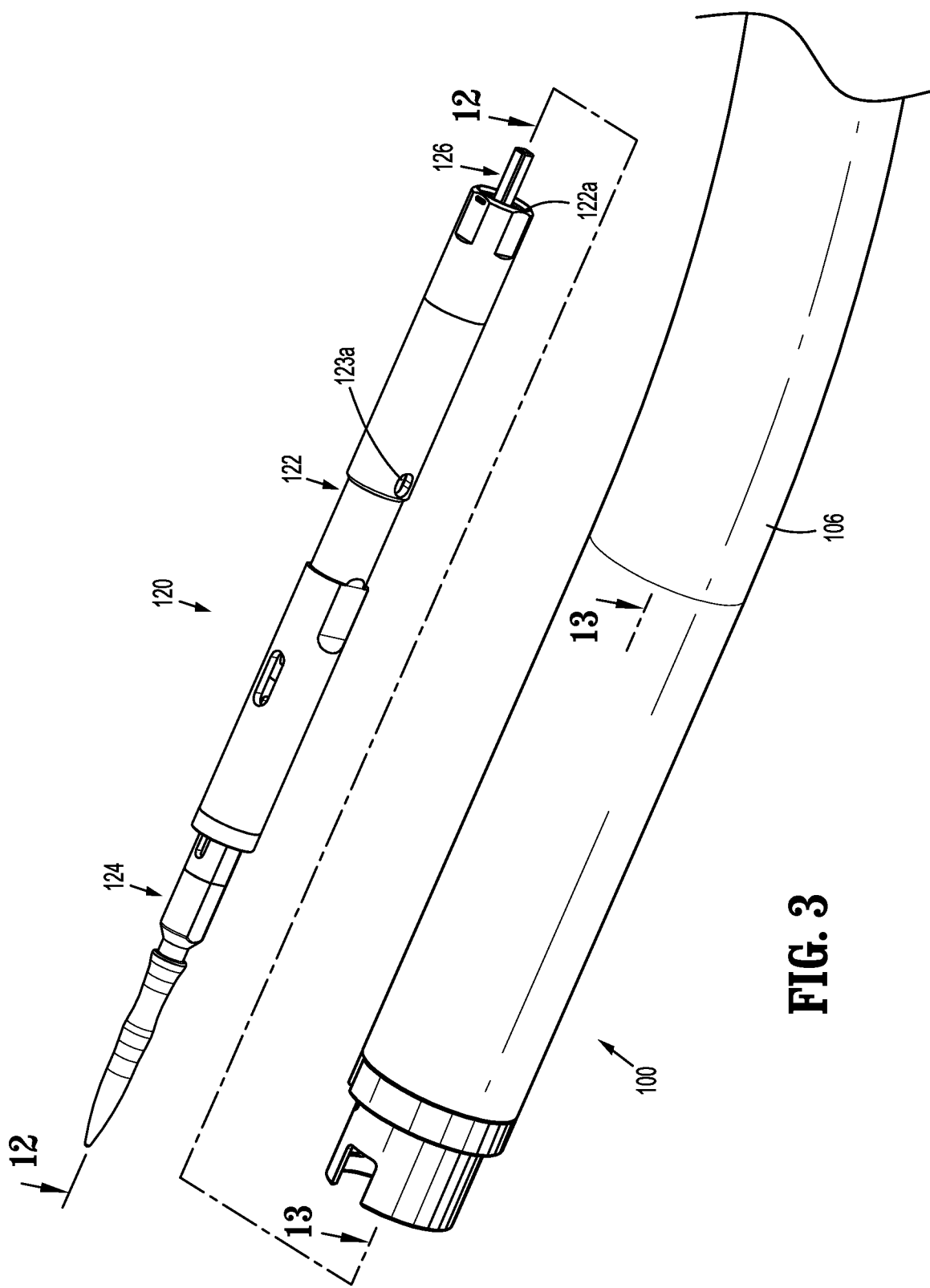
FIG. 3 is a perspective view of the distal end of the adapter assembly and the trocar assembly shown in FIG. 2, with the trocar assembly separated from the adapter assembly.

FIG. 3 illustrates the adapter assembly 100 including an outer sleeve 106, and a connector housing 108 secured to a distal end of the outer sleeve 106. The connector housing 108 is configured to releasably secure an end effector, e.g., the end effector 30 (FIG. 1), to the adapter assembly 100. A drive assembly 110 (FIG. 16) including first and second drive assemblies 112, 114 extends through the outer sleeve 106 of the adapter assembly 100. For a detailed description of the structure and function of an exemplary drive assembly, please refer to the '254 patent.

The adapter assembly 100 further includes a trocar assembly 120, and a retaining mechanism 130 releasably securing the trocar assembly 120 relative to the outer sleeve 106 of the adapter assembly 100. The trocar assembly 120 will only be described to the extent necessary to describe the aspects of the disclosure. For a detailed description of the structure and function of an exemplary trocar assembly, please refer to the '254 patent.

Figure 12:
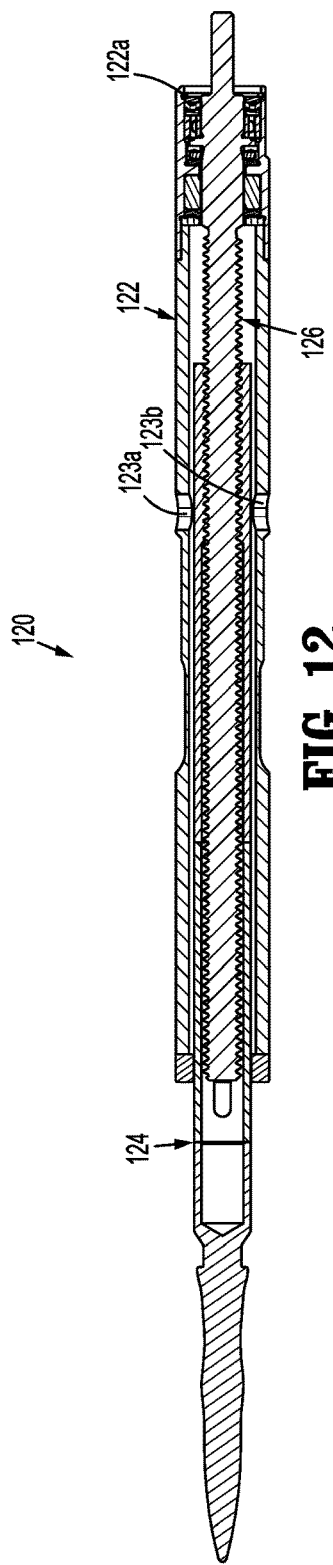
FIG. 12 is a cross-sectional top view of the trocar assembly shown in FIGS. 2 and 3, taken along section line 12-12 shown in FIG. 3.

FIG. 3 illustrates the trocar assembly 120 of the adapter assembly 100 (FIG. 2) including a trocar housing 122, a trocar member 124 slidably disposed within the trocar housing 122, and a drive screw 126 operably received within the trocar member 124 for axially moving the trocar member 124 relative to the trocar housing 122. The trocar housing 122 defines first and second locking openings 123a, 123b (FIG. 12) for receiving respective free ends 146a, 146b of first and second retention members 140a, 140b (FIG. 5) of the retaining mechanism 130 of the adapter assembly 100.

Figure 4:
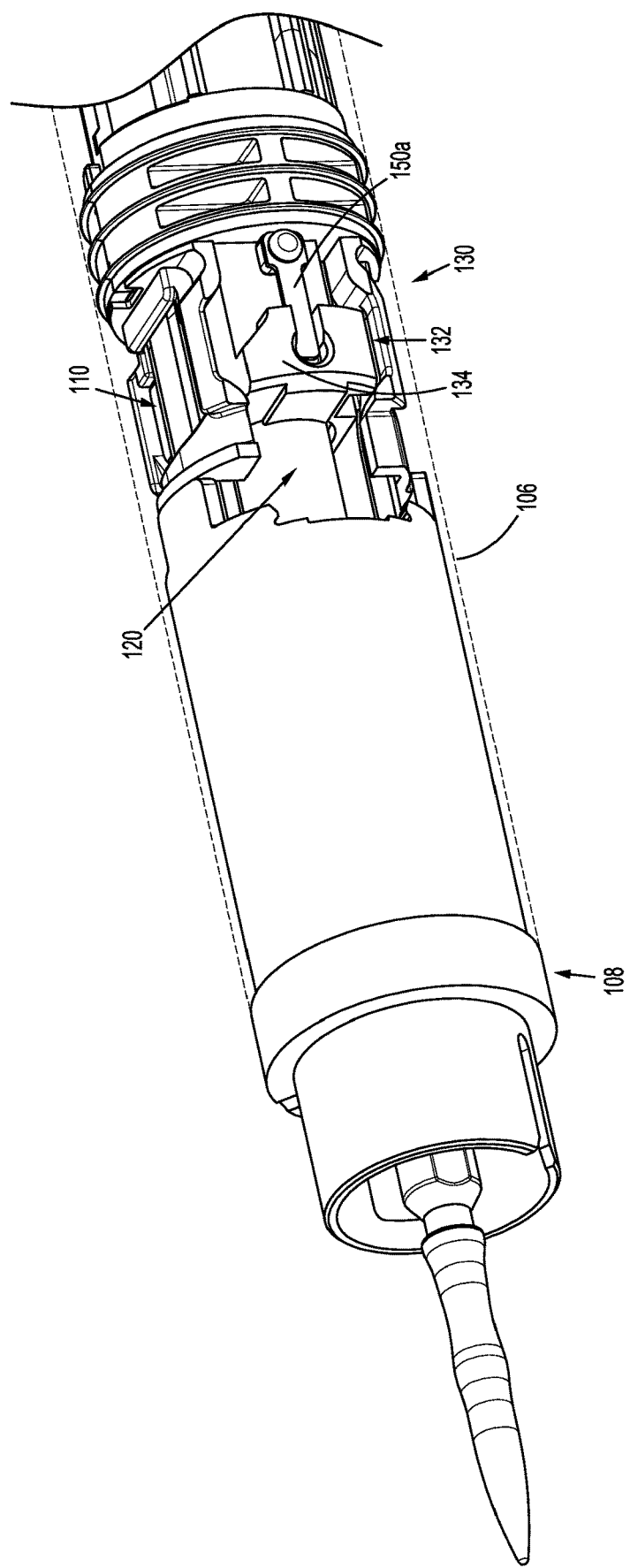
FIG. 4 is a side perspective view of the distal portion of the adapter assembly with an outer sleeve removed to expose a retaining mechanism.
Figure 5:
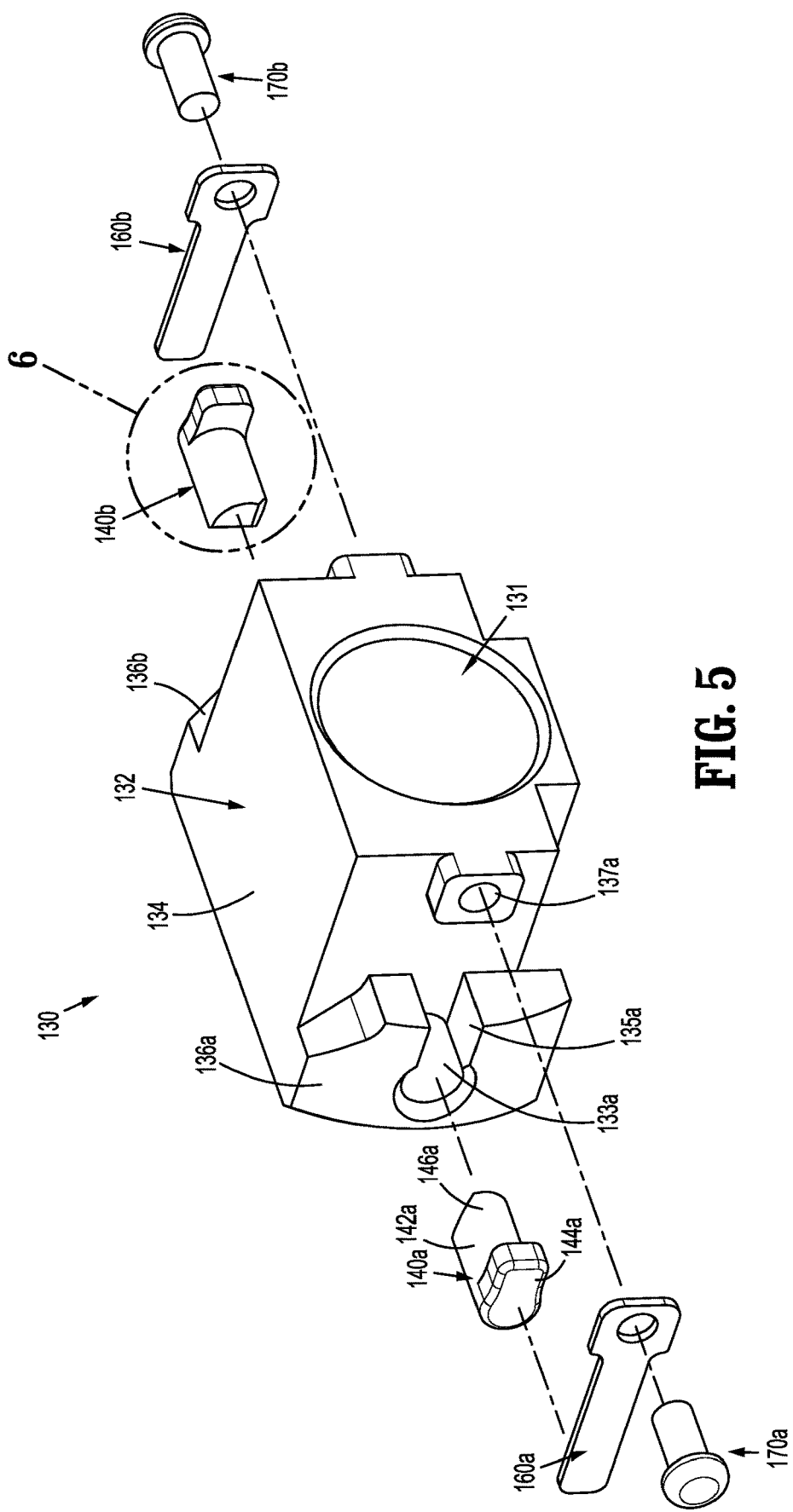
FIG. 5 is a side perspective view of the retaining mechanism shown in FIG. 4, with components separated.
Figure 6:
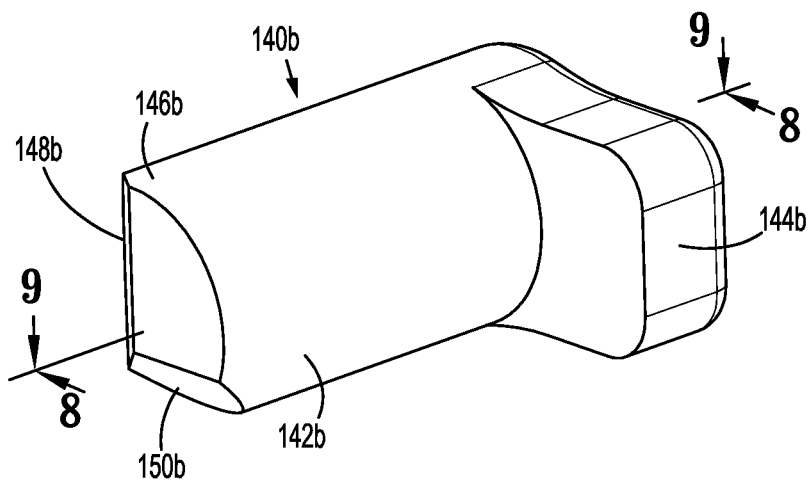
FIG. 6 is a side perspective view of a retention member of the retaining mechanism shown in FIGS. 4 and 5.
Figure 7:
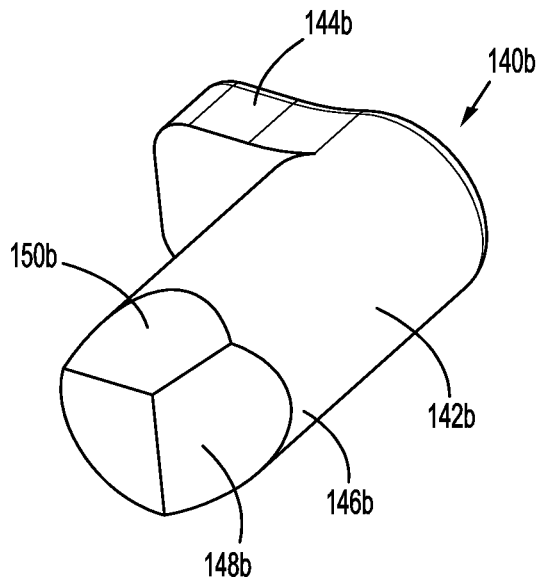
FIG. 7 is a side perspective view of the retention member shown in FIG. 6, rotated about a longitudinal axis one-hundred eighty degrees (180°)
Figure 8:
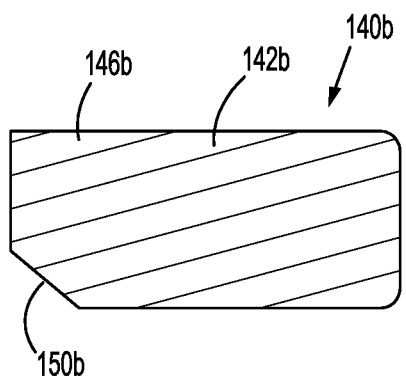
FIG. 8 is a cross-sectional side view the retention member shown in FIGS. 6 and 7, taken along section line 8-8 shown in FIG. 6.
Figure 9:
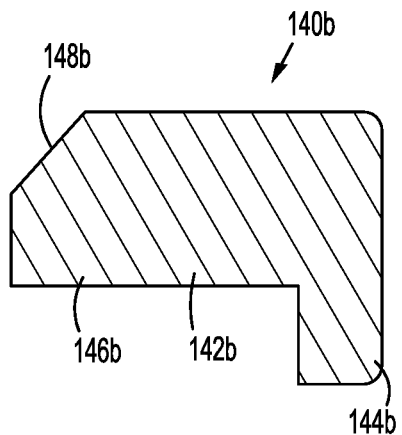
FIG. 9 is a cross-sectional top view of the retention member shown in FIGS. 6-8, taken along section line 9-9 shown in FIG. 6.

FIG. 5 shows the retaining mechanism 130 of the adapter assembly 100 including a housing 132 supported within the outer sleeve 106 (FIG. 4) of the adapter assembly 100, first and second retention members 140a, 140b operably supported within the housing 132 and configured for selective receipt within the first and second locking openings 123a, 123b in the trocar housing 122 of the trocar assembly 120, and first and second biasing members, e.g., first and second leaf springs 160a, 160b, secured to the housing 132 and in operable engagement with the respect first and second retention members 140a, 140b.

The housing 132 of the retaining mechanism 130 includes a body portion 134 defining a longitudinal opening 131 for receipt of the trocar assembly 120 and first and second flange portions 136a, 136b. The first and second flange portions 136a, 136b each define a cylindrical opening 133a, 133b in communication with the longitudinal openings 131 in the body portion 134 and a slot 135a, 135b extending from the respective first and second cylindrical openings 133a, 133b. The first and second cylindrical openings 133a, 133b and the first and second slots 135a, 135b operably receive the respective first and second retention members 140a, 140b. In embodiments, and as shown, the body portion 134 of the housing 132 further defines a pair of openings 137a, 137b for receiving respective first and second pins 170a, 170b, which secure the respective first and second leaf springs 160a, 160b to the housing 132.

FIGS. 6-9 illustrate the first and second retention members 140a (FIG. 5), 140b of the retaining mechanism 130 each including body portion 142a (FIG. 5), 142b, respectively, and a tab portion 144a (FIG. 5), 144b, respectively, extending from the respective body portions 142a, 142b. Free ends 146a (FIG. 5), 146b of the respective first and second retention members 140a, 140b include a first cam surface 148a (FIG. 13), 148b, respectively, and a second cam surface 150a (FIG. 16), 150b. The first cam surfaces 148a, 148b of the respective first and second retention members 140a, 140b are configured to facilitate loading of the trocar assembly 120 within the adapter assembly 100 (FIG. 2). More particularly, the first cam surfaces 148a, 148b face in a distal direction when secured within the housing 132 of the retaining mechanism 130 and are configured to engage a proximal portion 122a (FIG. 3) of the trocar housing 122 of the trocar assembly 100 during loading of the trocar assembly 120 within the adapter assembly 100. Engagement of the proximal portion 122a of the trocar housing 122 with the first cam surfaces 148a, 148b causes the respective first and second retention members 140a, 140b to move radially outwardly.

The second cam surfaces 150a, 150b of the respective first and second retention members 140a, 140b are configured to facilitate release of the trocar assembly 120 from within the adapter assembly 100. More particularly, the second cam surfaces 150a, 150b face in a circumferential direction and are configured to engage the trocar housing 122 when the trocar assembly 120 is rotated about a longitudinal axis "x" of the distal portion 104 (FIG. 2) of the adapter assembly 100. Engagement of the second cam surfaces 150a, 150b with the trocar housing 122 as the trocar assembly 100 is being rotated causes the first and second retention members 140a, 140b to move radially outwardly.

Figure 11:
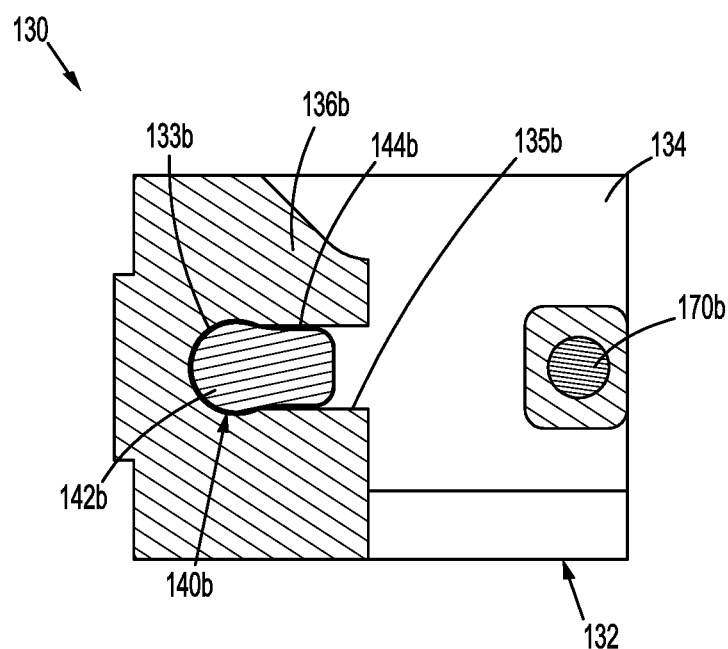
FIG. 11 is a cross-sectional side view taken along section line 11-11 shown in FIG. 10.

FIG. 11 illustrates that the tab portions 144a, 144b of the first and second retention members 140a, 140b of the retaining mechanism 130 are operably received within the respective first and second slots 135a, 135b of the housing 132 of the retaining mechanism 130 while the body portions 142a, 142b are operably received within the respective first and second cylindrical openings 133a, 133b of the housing 132. Receipt of the tab portions 144a, 144b of the respective first and second retention members 140a, 140b within the respective first and second slots 135a, 135b in the housing 132 rotationally secures the first and second retention members 140a, 140b relative to the housing 132. In this manner, the first and second retention members 140a, 140b are maintained in a fixed orientation relative to a longitudinal axis "x" of the distal portions 104 of the adapter assembly 100. Alternatively, the body portions 142a, 142b of the respective first and second retention members 140a, 140b include an oval, rectangular, or other non-circular cross-section that would prevent rotation of the first and second retention members 140a, 140b within the housing 132.

Figure 10:
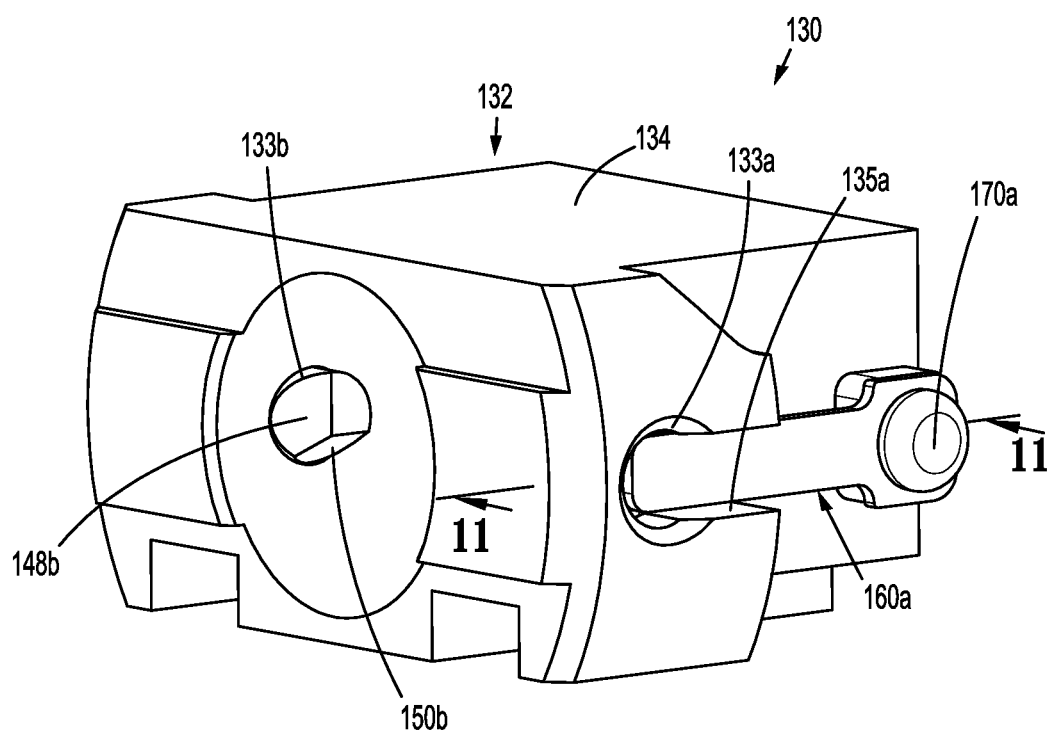
FIG. 10 is side perspective view of the retaining mechanism shown in FIGS. 4 and 5, in a first or locked position.

The first and second retention members 140a, 140b of the retaining mechanism 130 are retained within the respective first and second cylindrical openings 133a, 133b in the housing 132 of the retaining mechanism 130 by the first and second leaf springs 160a (FIG. 10), 160b (FIG. 5), respectively. As noted above, the first and second leaf springs 160a, 160b are secured to the housing by 132 the respective first and second pins 170a (FIG. 10), 170b (FIG. 11). Although shown secured to the housing 132 with pins 170a, 170b, it is envisioned that the first and second leaf springs 160a, 160b may be secured to the housing 132 in any suitable manner, including, for example, by welding, using adhesives, with mechanical and/or chemical fasteners, or via friction fit.

Figure 13:
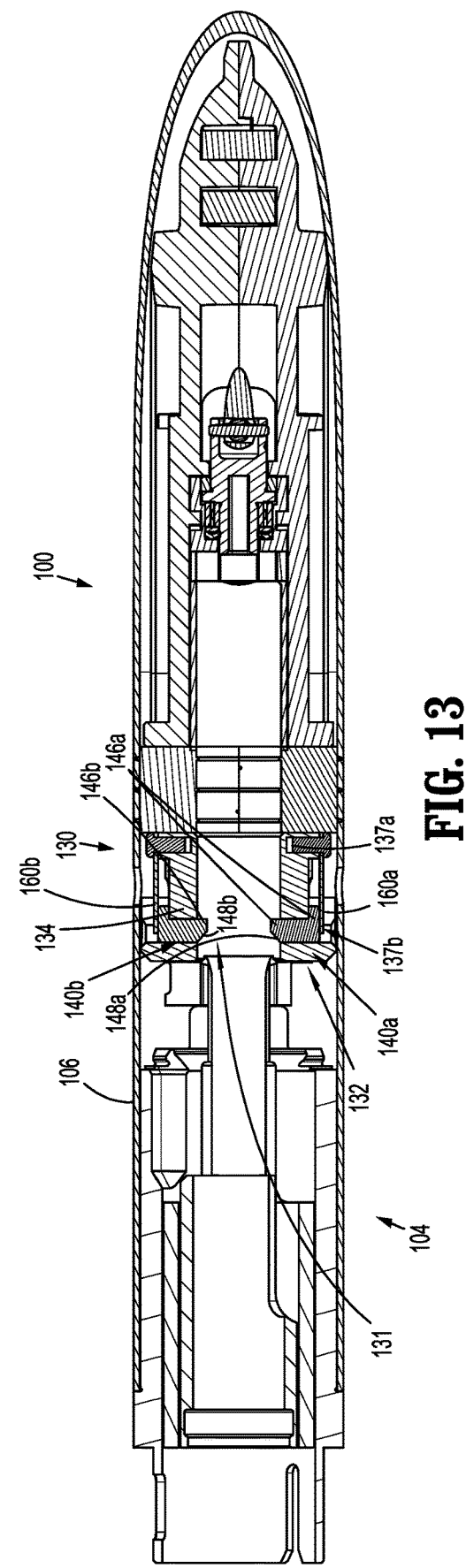
FIG. 13 is a cross-sectional top view of the adapter assembly shown in FIGS. 1-3, taken along section line 13-13 shown in FIG. 3.

FIG. 13 illustrates the adapter assembly 100 prior to loading of the trocar assembly 120 (FIG. 12) within the distal portions 104 of the adapter assembly 100. In this manner, the first and second retention members 140a, 140b of the retaining mechanism 130 are in their first or initial positions, with the free ends 146a, 146b, respectively, extending within the longitudinal passage 131 of the housing 132 of the retaining mechanism 130.

Figure 14:
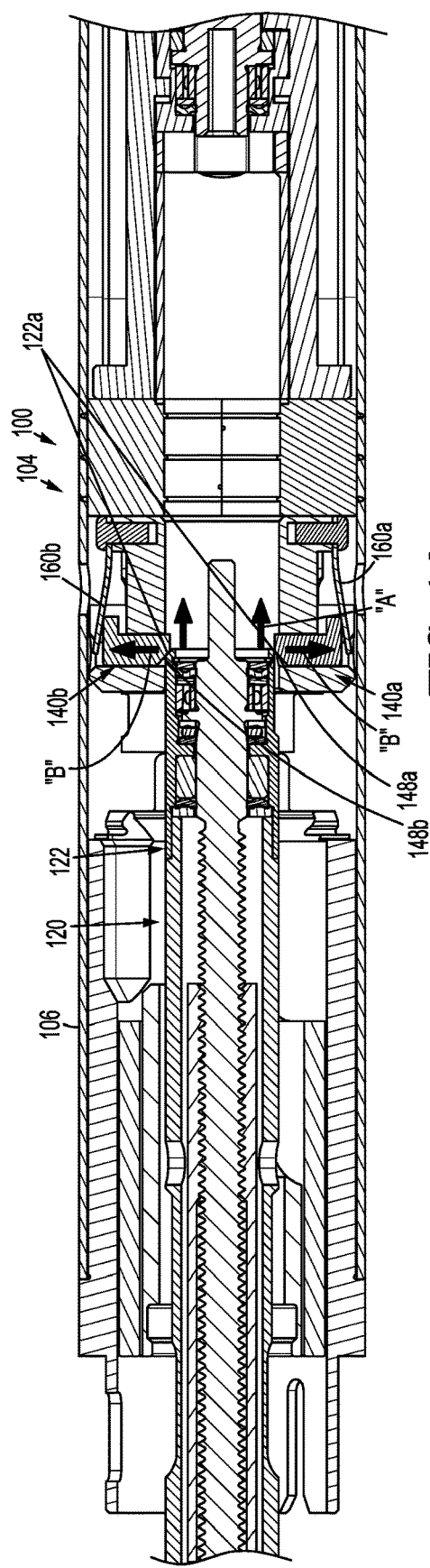
FIG. 14 is a cross-sectional side view of the adapter assembly shown in FIGS. 1-3, including the trocar assembly shown in FIGS. 2 and 3 partially received within the adapter assembly.

FIG. 14 illustrates the trocar assembly 120 in a first rotational orientation relative to a longitudinal axis "x" of the distal portion 104 of the adapter assembly 100 as the trocar assembly 120 is loaded within the distal portion 104 of the adapter assembly 100 and moves through the longitudinal passage 131 in the housing 132 of the retaining mechanism 130, as indicated by arrows "A". As the trocar assembly 120 is loaded, the leading end 122a of the trocar housing 122 of the trocar assembly 120 engages the first cam surfaces 148a, 148b of the respective first and second retention members 140a, 140b. Engagement of the first and second cam surfaces 148a, 148b by the proximal portion 122a of the trocar housing 122 causes the first and second retention members 140a, 140b to move radially outward, as indicated by arrows "B", against the bias of the respective leaf springs 160a, 160b.

Figure 15:
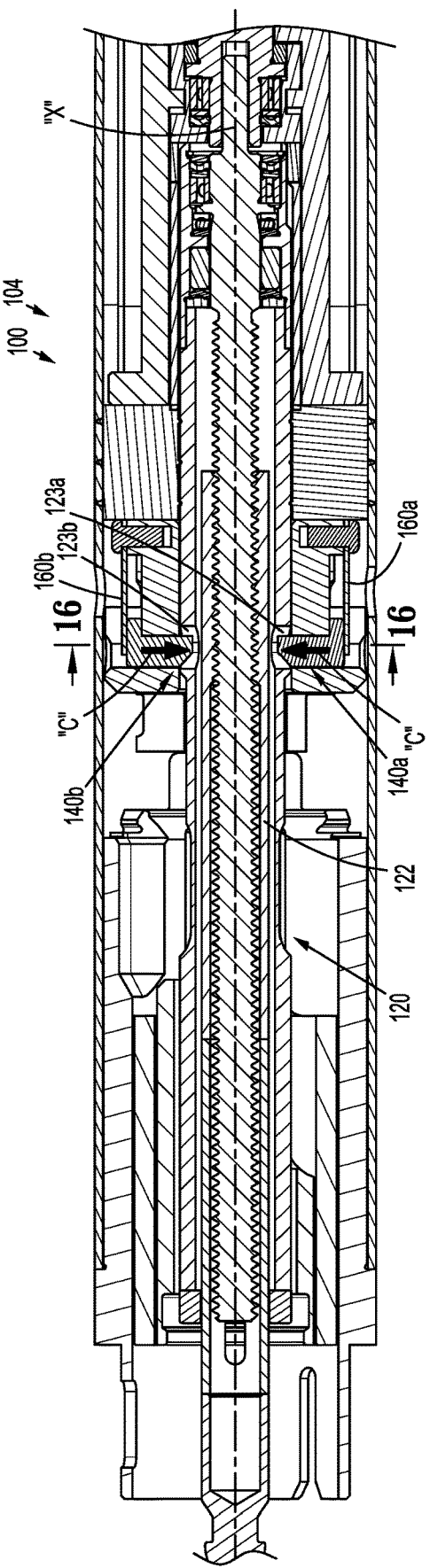
FIG. 15 is the cross-sectional side view of the adapter assembly and trocar assembly shown in FIG. 14, with trocar assembly fully received within the adapter assembly.
Figure 16:
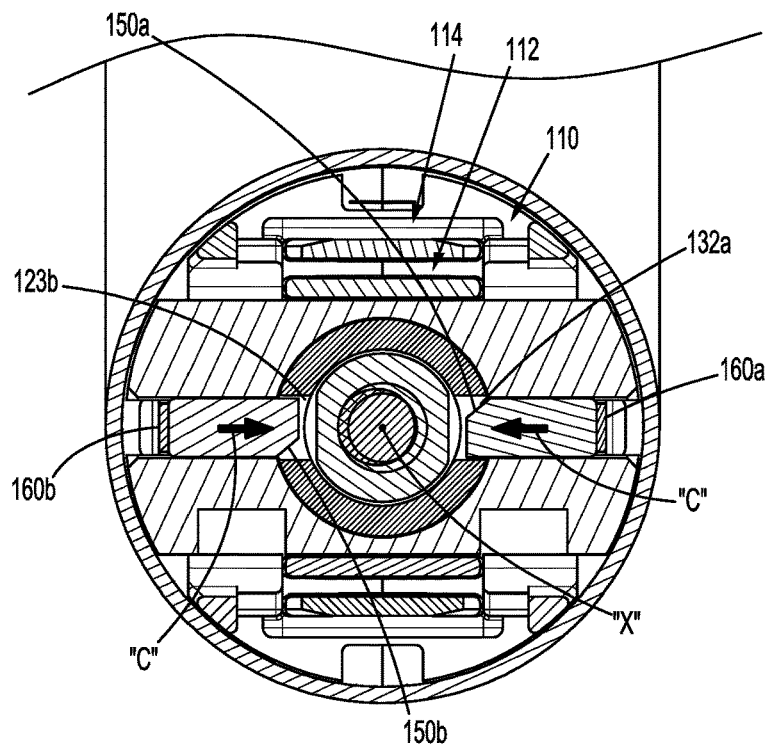
FIG. 16 is a cross-sectional end view of the adapter assembly shown in FIG. 15, taken along section line 16-16 shown in FIG. 15, with the trocar assembly fully received within the adapter assembly.

FIGS. 15 and 16 illustrate the trocar assembly 120 fully received within the distal portion 104 of the adapter assembly 100 with the first and second locking openings 123a, 123b in the trocar housing 122 of the trocar assembly 120 aligned with the respective first and second retention members 140a, 140b of the retaining mechanism 130. When the trocar assembly 120 is fully received within the distal portion 104 of the adapter assembly 100, the bias of the first and second leaf springs 160a, 160b on the respective first and second retention members 140a, 140b of the retaining mechanism 130 causes the first and second retention members 140a, 140b to move radially inward into the respective first and second locking openings 123a, 123b of the trocar housing 122, as indicated by arrows "C". Receipt of the first and second retention members 140a, 140b within the respective first and second locking openings 123a, 123b secures the trocar assembly 120 within the adapter assembly 100.

Figure 17:
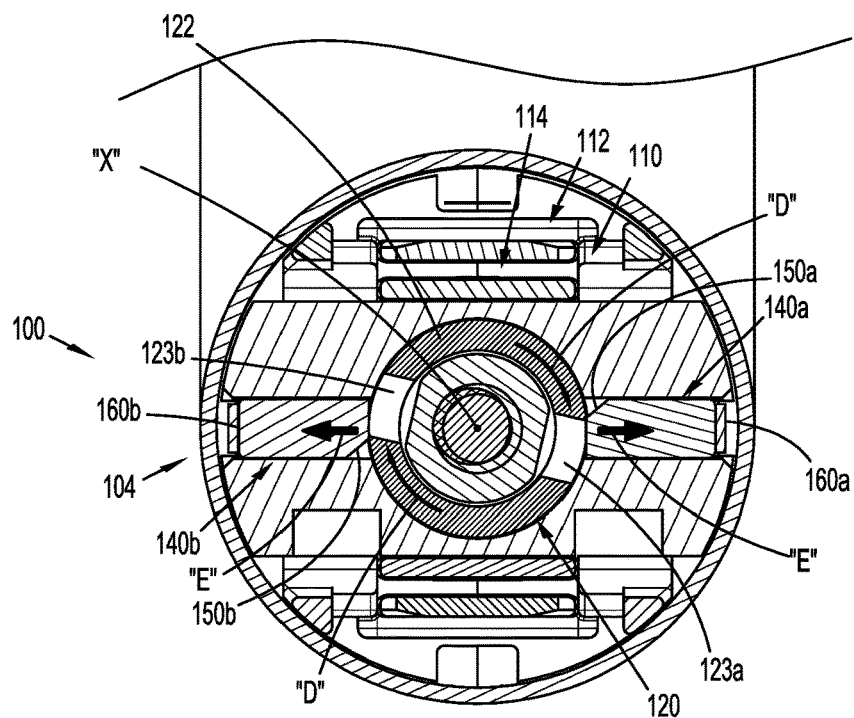
FIG. 17 is the cross-sectional end view of the adapter assembly and trocar assembly shown in FIG. 16, with the trocar assembly in a rotated position.
Figure 18:
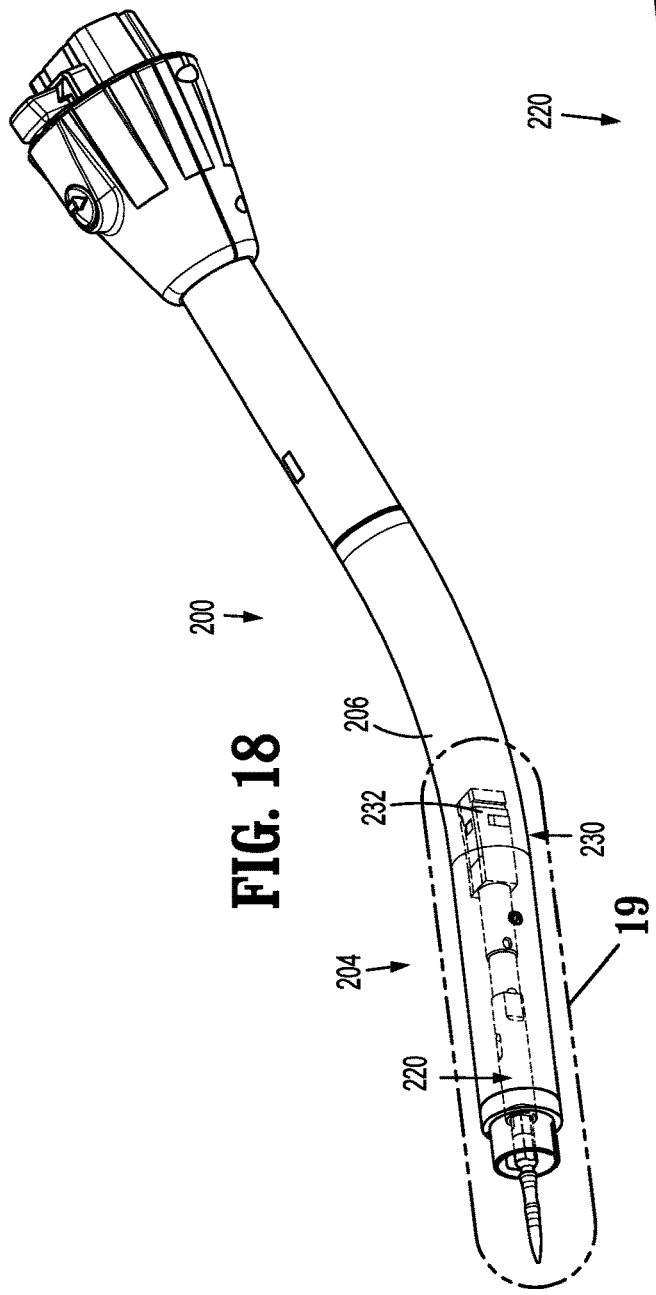
FIG. 18 is a side perspective view of an adapter assembly according to another exemplary embodiment of the disclosure, including a trocar assembly secured within the adapter assembly by a retaining mechanism.
Figure 19:
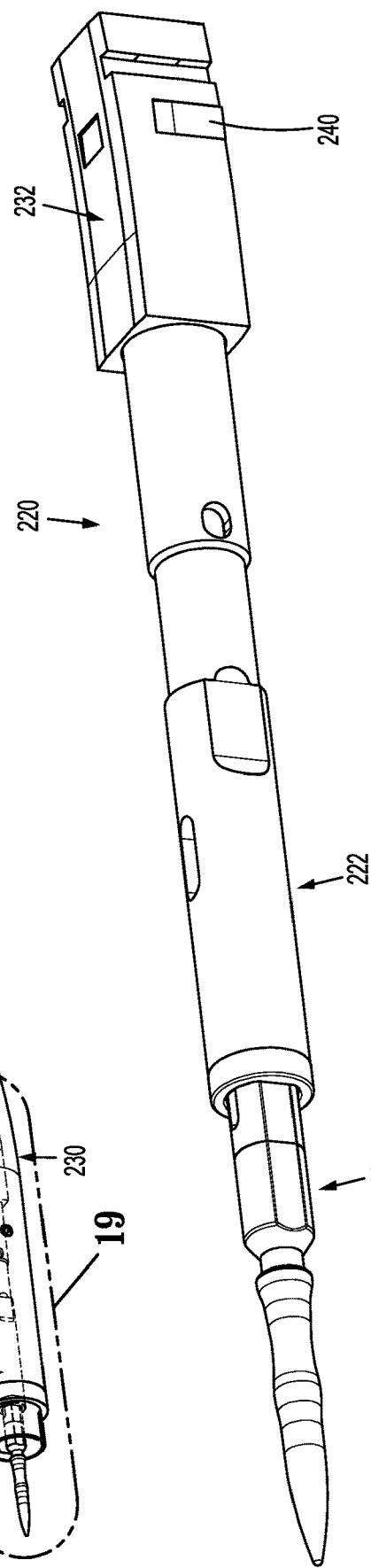
FIG. 19 is an enlarged view of the indicated area of detail shown in FIG. 18, including the trocar assembly and the retaining mechanism shown in FIG. 18.

Subsequent to use of the adapter assembly 100, or when otherwise desired to remove the trocar assembly 120 from within the adapter assembly 100, the trocar assembly 120 may be withdrawn from the adapter assembly 100 by rotating the trocar assembly 120 about the longitudinal axis "x" of the distal portion 104 of the adapter assembly 100. More particularly, as shown in FIG. 17, when the trocar assembly 120 is rotated about the longitudinal axis "x", as indicated by arrows "D", the trocar housing 122 of the trocar assembly 120 engages the second cam surfaces 150a, 150b of the respective first and second retention members 140a, 140b of the retaining mechanism 130. Engagement of the second cam surfaces 150a, 150b of the respective first and second retention members 140a, 140b causes the first and second retention members 140a, 140b to move radially outward, against the bias of the respective first and second leaf springs 160a, 160b, as indicated by arrows "E". It is envisioned that the trocar assembly 130 may include a feature (not shown) for engagement by a clinician or other personnel, directly, and/or with the assistance of a removal tool (not shown) for facilitating rotation of the trocar assembly 130 about the longitudinal axis "x", and/or for facilitating withdrawal of the trocar assembly 130 from within the distal portion 104 of the adapter assembly 100.

Once the first and second retention members 140a, 140b of the retaining mechanism 130 are completely withdrawn from within the respective first and second locking openings 123a, 123b in the trocar housing 122 of the trocar assembly 120, the trocar assembly 120 may be removed from within the distal portion 104 of the adapter assembly 100.

FIGS. 18-29 illustrate an adapter assembly 200 including a retaining mechanism 230 according to another exemplary aspect of the disclosure for releasably securing a trocar assembly 220 within a distal portion 204 of the adapter assembly 200. The adapter assembly 200 is substantially similar to the adapter assembly 100 described hereinabove, and will only be described in detail as relates to the differences.

FIGS. 18-23 illustrate the trocar assembly 220 including a trocar housing 222, a trocar member 224 slidably disposed within the trocar housing 222, and a drive screw 226 (FIG. 21) operably received within the trocar member 224 for axially moving the trocar member 224 relative to the trocar housing 222. A proximal portion 222a of the trocar housing 222 defines a semi-annular groove 227, and includes first, second, and third flat section 228a, 228b, 228c (collectively, a plurality of flat sections 228) formed proximal of the semi-annular groove 227. The first, second, and third flat section 228a, 228b, 228c are spaced bout the outer surface of the proximal portion 222a of the trocar housing 222. The semi-annular groove 227 and the plurality of flat sections 228 of the trocar housing 222 are configured for releasable engagement of the trocar assembly 220 within an insert member 240 of the retaining mechanism 230.

Figure 20:
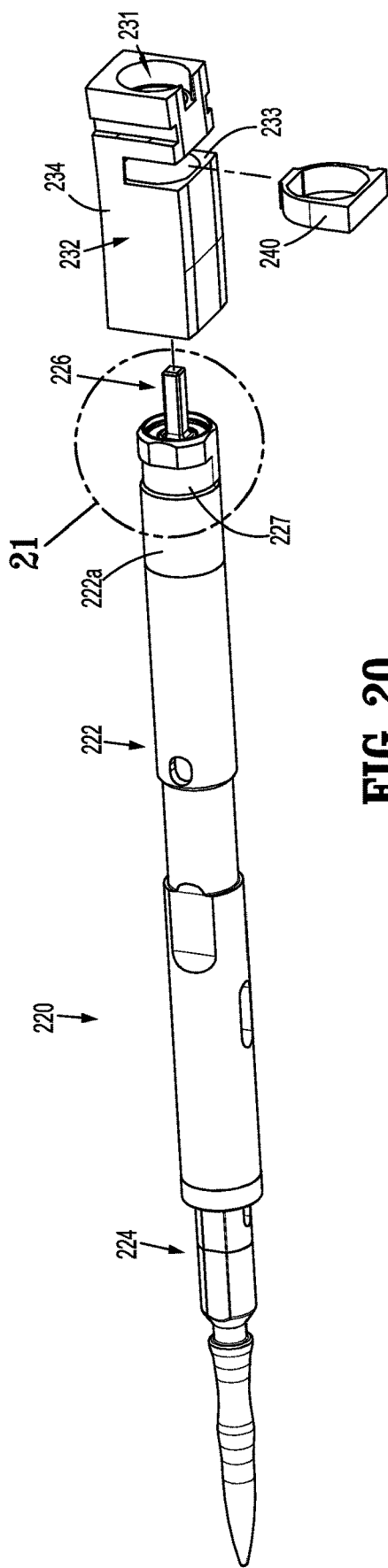
FIG. 20 is a side perspective view of the trocar assembly and the retaining mechanism shown in FIG. 18, with components of the retaining mechanism separated.
Figure 22:
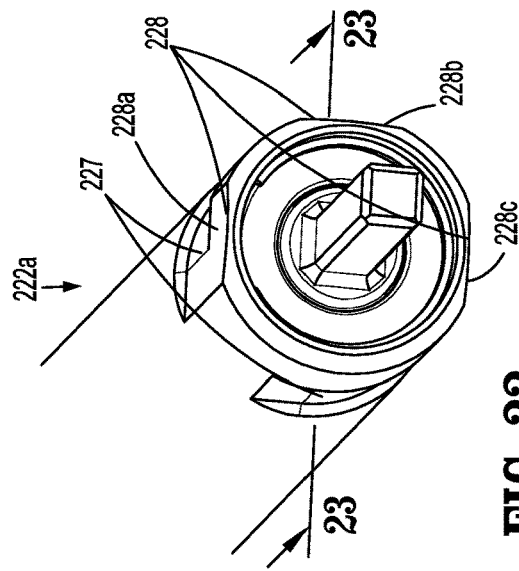
FIG. 22 is a perspective view of a proximal end of the trocar assembly shown in FIGS. 18-20.
Figure 21:
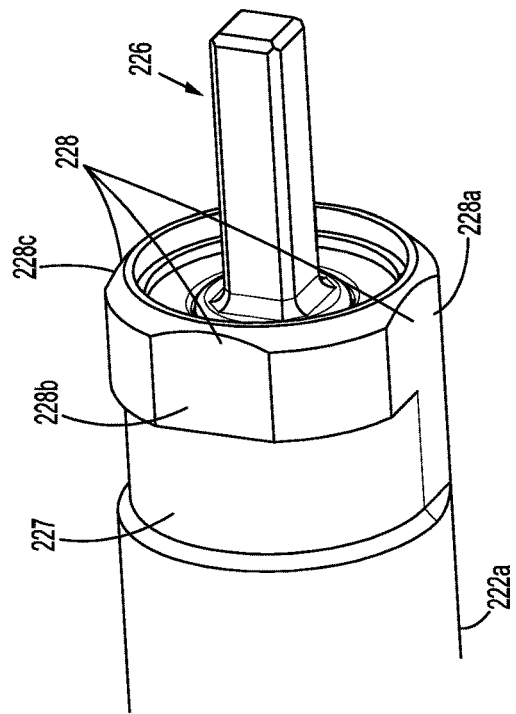
FIG. 21 is an enlarged view of the indicated area of detail shown in FIG. 20.
Figure 23:
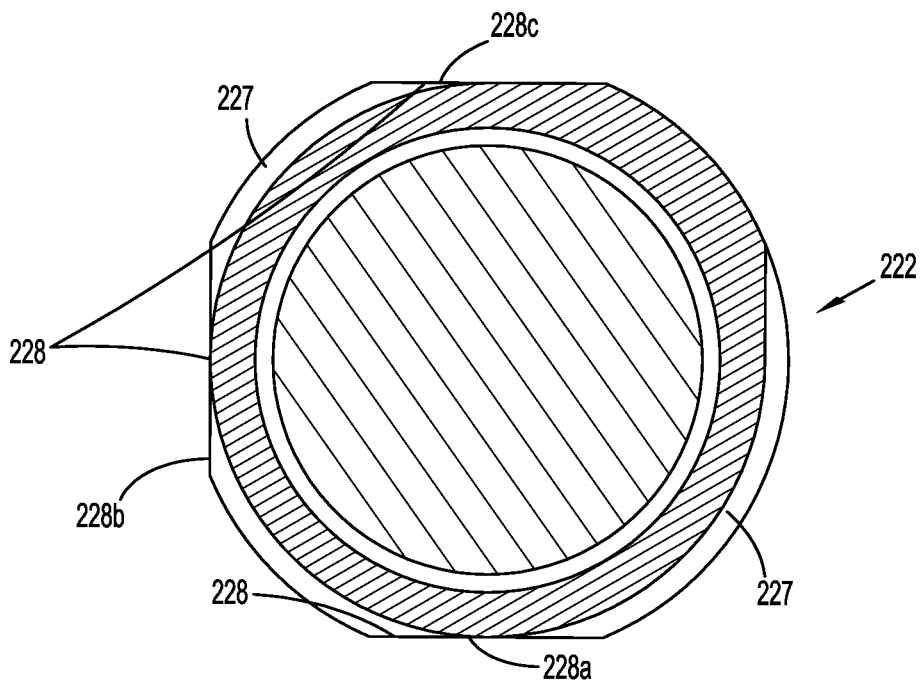
FIG. 23 is a cross-sectional end view of the trocar assembly shown in FIGS. 18-20, taken along section line 23-23 shown in FIG. 22.

FIG. 20 illustrates the retaining mechanism 230 of the adapter assembly 200 including a yoke or housing 232 and the insert member 240. The housing 232 includes a substantially rectangular body 234 defining a longitudinal passage 231 for receiving the proximal portion 222a of the trocar housing 222 of the trocar assembly 220, and a cutout 233 in communication with the longitudinal passage 231 for receiving the insert member 240.

Figure 24:
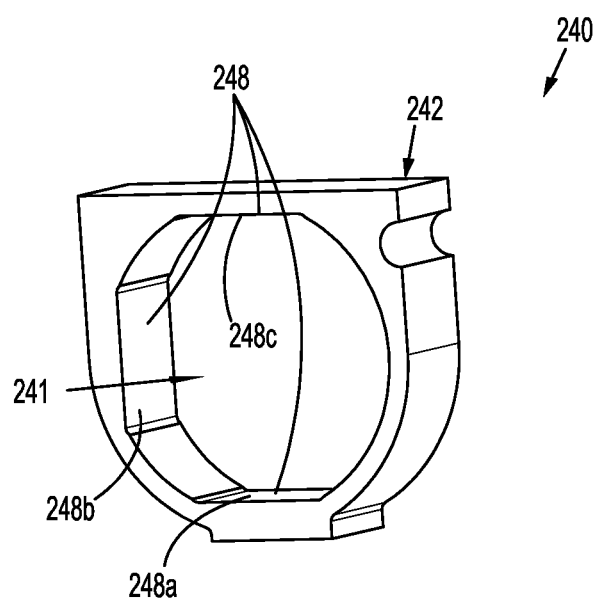
FIG. 24 is a side perspective view of an insert member of the retaining mechanism shown in FIGS. 18-20.

FIG. 24 illustrates the insert member 240 of the retaining mechanism 240. The insert member 240 includes a substantially D-shaped body 242 configured to be received within the cutout 233 in the trocar housing 222 of the trocar assembly 230. The insert member 240 defines an opening 241 for receipt of the proximal portion 222a of the trocar housing 222 of the trocar assembly 220. The insert member 240 includes first, second, and third flat sections 248a, 248b, 248c (collectively, a plurality of flat sections 248). The plurality of flat sections 228 of the trocar housing 222 correspond with the plurality of flat sections 248 of the insert member 240. More particularly, the first flat section 248a of the insert member 240 corresponds with the first flat section 228a of the trocar housing 222, the second flat section 248b of the insert member 240 corresponds with the second flat section 228b of the trocar housing 222, and the third flat section 248c of the insert member 240 corresponds with the third flat section 228c of the trocar housing 222.

Figure 25:
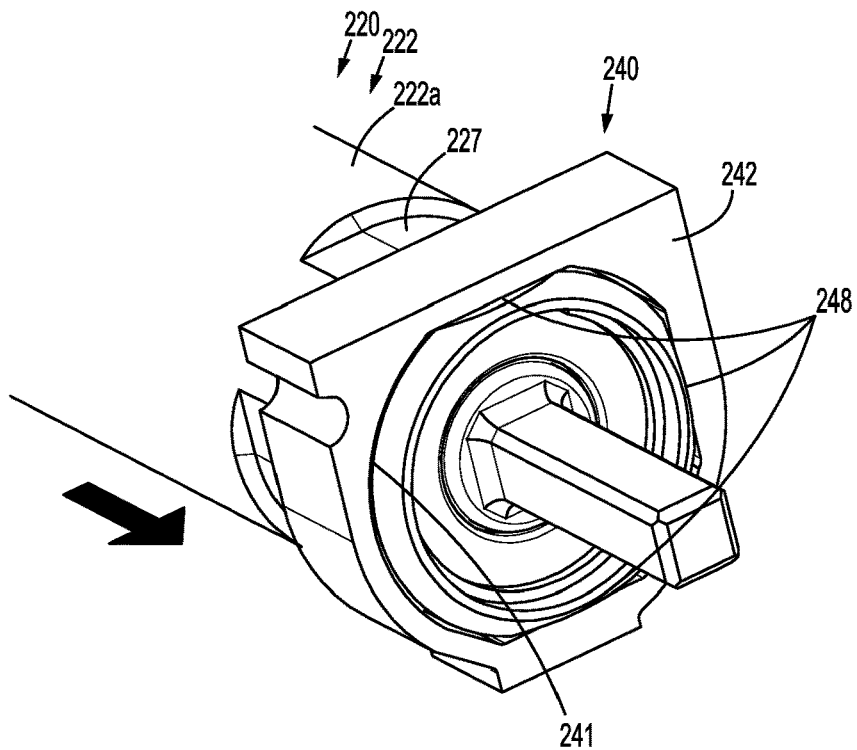
FIG. 25 is a perspective view of the proximal end of the trocar assembly shown in FIG. 22 and the insert member shown in FIG. 24, with the proximal end of the trocar assembly partially received though the insert member.
Figure 26:
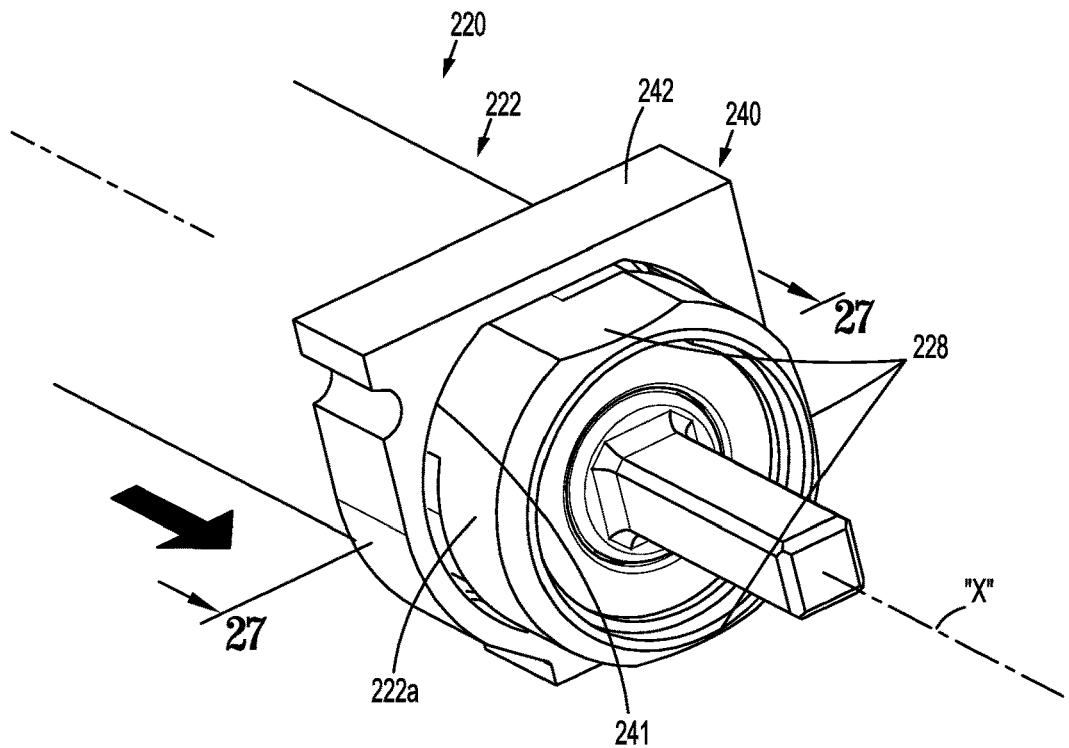
FIG. 26 is the end perspective view of the trocar assembly and insert member shown in FIG. 25, with the proximal end of the trocar assembly fully received though the insert member.
Figure 27:
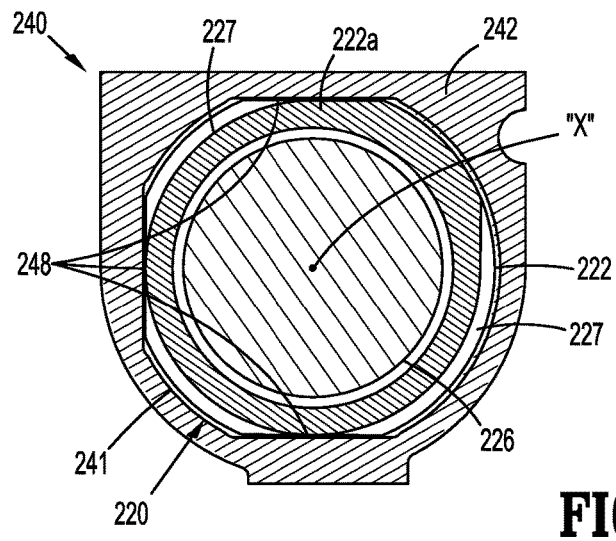
FIG. 27 is a cross-sectional end view of the trocar assembly and insert member shown in FIGS. 26 and 27, taken along section line 27-27 shown in FIG. 26, with the trocar assembly in an unlocked orientation.

FIGS. 25-27 illustrate the trocar assembly 220 in the first rotational orientation relative to the insert member 240. In the first rotational orientation, the plurality of flat sections 228 of the trocar housing 222 of the trocar assembly 220 align with the plurality of flat sections 248 of the insert member 240 of the retaining assembly 230 such that the trocar assembly 220 may be fully received through the opening 241 in the insert member 240.

FIG. 26 shows the trocar assembly 220 fully received through the opening 241 in the insert member 240, e.g., the semi-annular groove 227 in the trocar housing 222 of the trocar assembly 220 aligns with the insert member 240. In this manner, the trocar assembly 130 is able to be rotated about a longitudinal axis "x" of the distal portion 204 of the adapter assembly 200.

Figure 28:
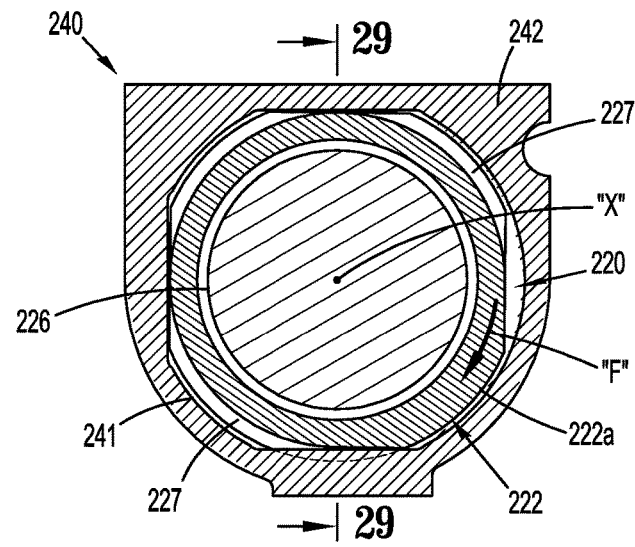
FIG. 28 is the cross-sectional end view of the trocar assembly and insert member shown in FIG. 27, with the trocar assembly in a locked orientation.
Figure 29:
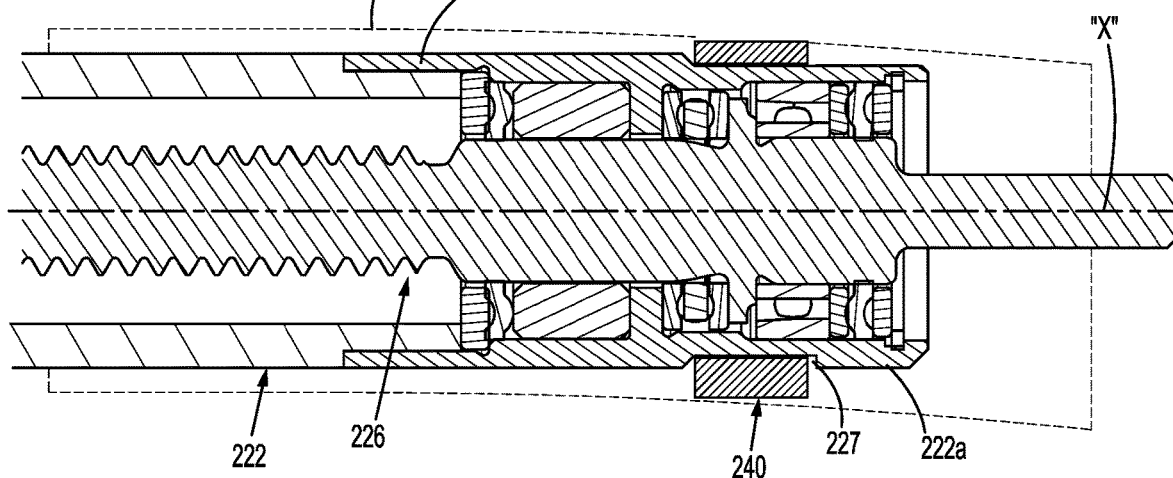
FIG. 29 is a cross-sectional side view of the trocar assembly and insert member shown in FIGS. 26-28, taken along section line 29-29 shown in FIG. 28.

FIGS. 28 and 29 illustrate the trocar assembly 220 in a second rotational orientation relative to the insert member 240 of the retaining assembly 230. More, particularly, the trocar assembly 220 has been rotated about the longitudinal axis "x" relative to the insert member 240 in a first direction, as indicated by arrow "F" in FIG. 28, to secure the trocar assembly 130 within the adapter assembly 200. In one aspect of the disclosure, the trocar assembly 220 is rotated ninety degrees (90°) about the longitudinal axis "x", between the first rotational orientation and the second rotational orientation.

In the second rotational orientation, the proximal portion 222a of the trocar housing 222 engages the insert member 240 of the retaining assembly 230 to secure the trocar assembly 230 within the distal portion 204 of the adapter assembly 200.

Following use of the adapter assembly 200, the trocar assembly 220 may be rotated about the longitudinal axis "x" in a second direction to cause the release of the trocar assembly 220 from the distal portion 204 of the adapter assembly 200.

FIGS. 30-37 illustrate an adapter assembly 300 according to another aspect of the disclosure. The adapter assembly 300 includes an outer sleeve 306, a retaining mechanism 330 according to another exemplary aspect of the disclosure disposed within a distal portion 304 of an elongate body of the adapter assembly 300, and a trocar assembly 320 releasably securable within the distal portion 304 of the adapter assembly 300.

Figure 32:
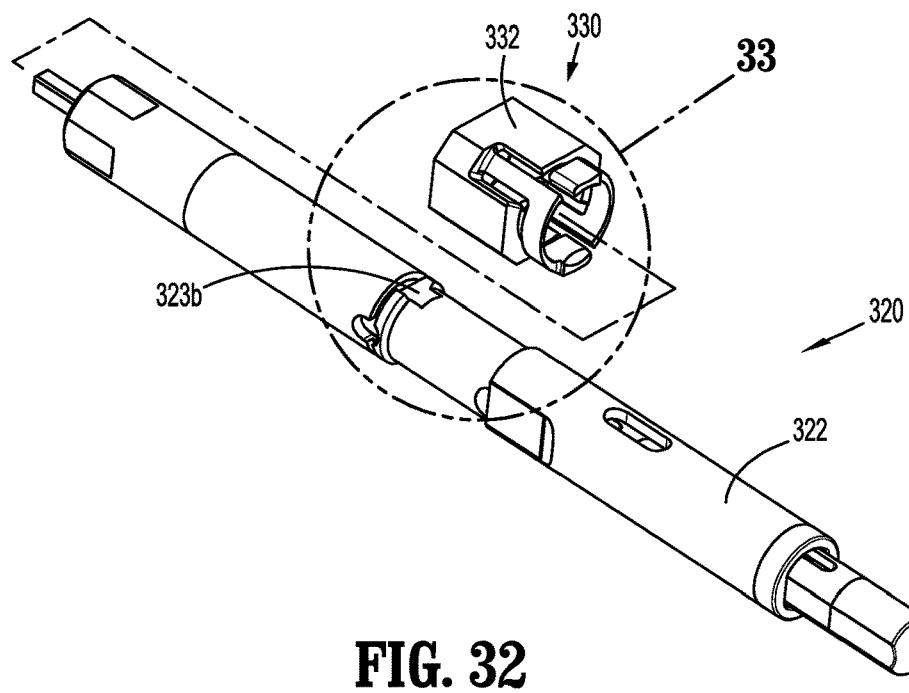
FIG. 32 is a perspective view of the trocar assembly and the retaining mechanism shown in FIGS. 30-32, with parts separated.
Figure 33:
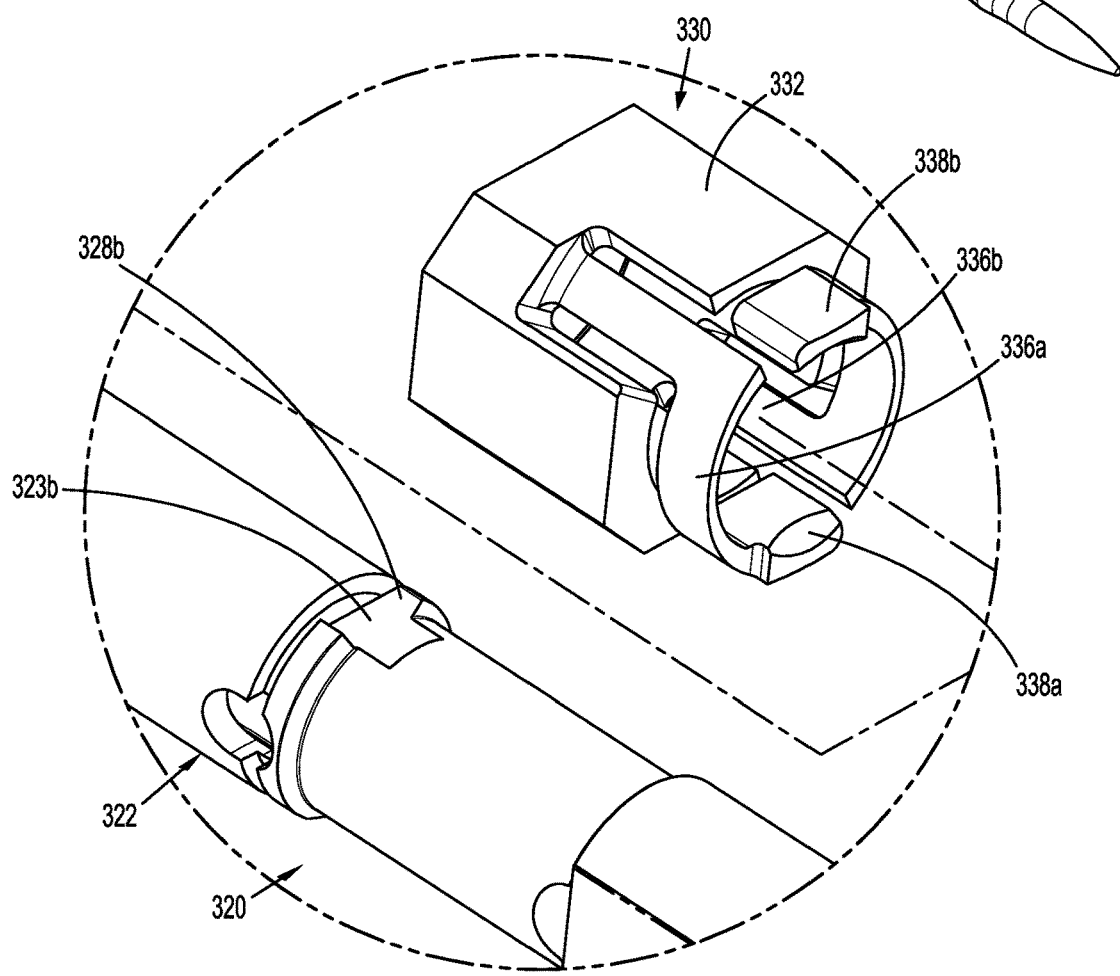
FIG. 33 is an enlarged view of the indicated area of detail shown in FIG. 33.
Figure 34:
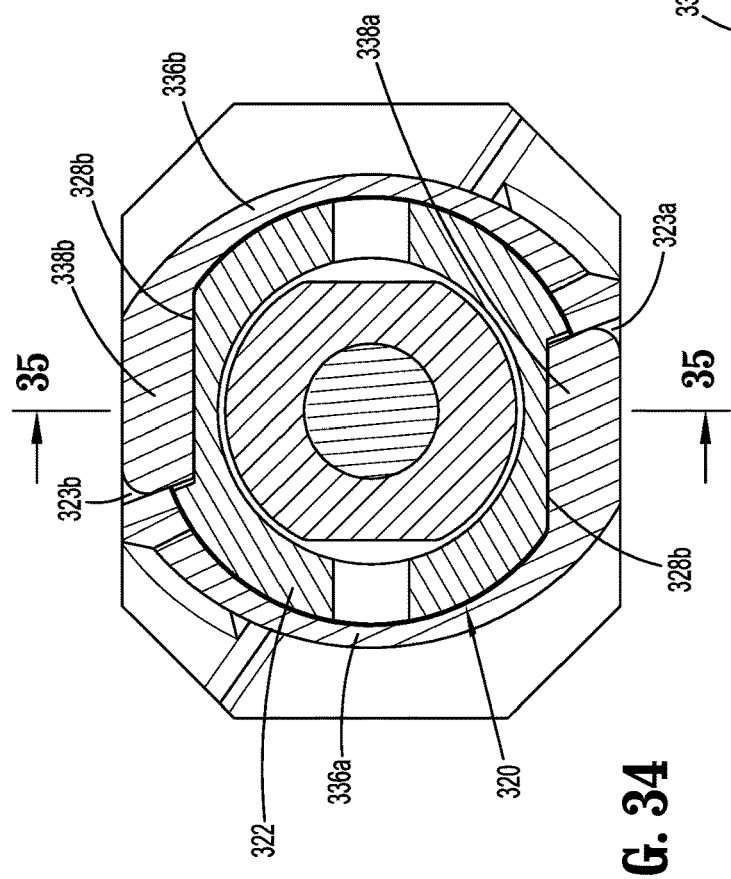
FIG. 34 is a cross-sectional end view of the trocar assembly and the retaining mechanism shown in FIGS. 30-33, taken along section line 34-34 shown in FIG. 31, with the retaining mechanism in a locked condition.

FIGS. 32-34 illustrate first and second cutouts 323a, 323b (FIG. 34) in a trocar housing 322 of the trocar assembly 320. The first and second cutouts 323a, 323b in the trocar housing 322 are configured to receive locking portions 338a, 338b, respectively, of respective first and second arms 336a, 336b of the retainer mechanism 330. The first and second cutouts 323a, 323b (FIG. 34) in the trocar housing 322 are at least partially defined by cam surfaces 328a, 328b.

The retaining mechanism 330 includes a housing 332 having a substantially rectangular body 334 defining a longitudinal passage 331 for receiving the proximal portion 322a of the trocar housing 322 of the trocar assembly 320. The first and second arms 336a, 336b extend from the body 334 of the housing 332 of the retaining mechanism 330 and are cantilevered to an initial or lock position. The lock portions 338a, 338b are disposed on free ends of the first and second arms 336a, 336b. The lock portions 338a, 338b may include contoured and/or angled leading edges configured to engage the trocar housing 322 during receipt of the trocar assembly 320 into the distal portion 304 of the adapter assembly 300 to facilitate outward flexing of the first and second arms 336a, 336b and receipt of the trocar housing 322 within the longitudinal passage 331 of the retaining mechanism 330.

Figure 35:
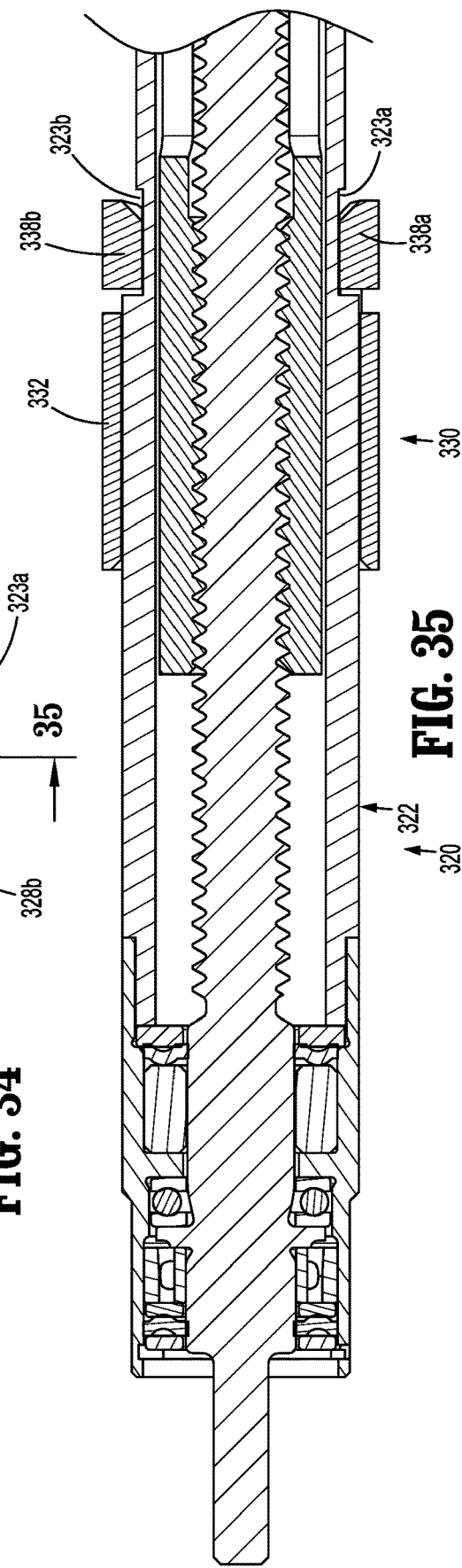
FIG. 35 is a cross-sectional side view of the trocar assembly and the retaining mechanism shown in FIGS. 30-34, taken along section line 35-35 shown in FIG. 34.

FIGS. 34 and 35 illustrate the trocar assembly 320 fully received within the distal portion 304 of the adapter assembly 300 in a first rotational orientation relative to the longitudinal axis "x" of the distal portion 304 of the adapter assembly 300, and the retaining mechanism 330 of the adapter assembly 300 in a locked configuration. When the trocar assembly 320 is fully received within the distal portion 304 of the adapter assembly 300 and the retaining mechanism 330 is in the locked configuration, the lock portions 338a, 338b of the respective first and second arms 336a, 336b of the retaining mechanism 330 are received within respective first and second cutouts 323a, 323b in the trocar housing 322 of the trocar assembly 320. Receipt of the lock portions 348a, 348b of the respective first and second arms 346a, 346b within the respective first and second cutouts 323a, 323b secures the trocar assembly 320 within the adapter assembly 300.

Figure 36:
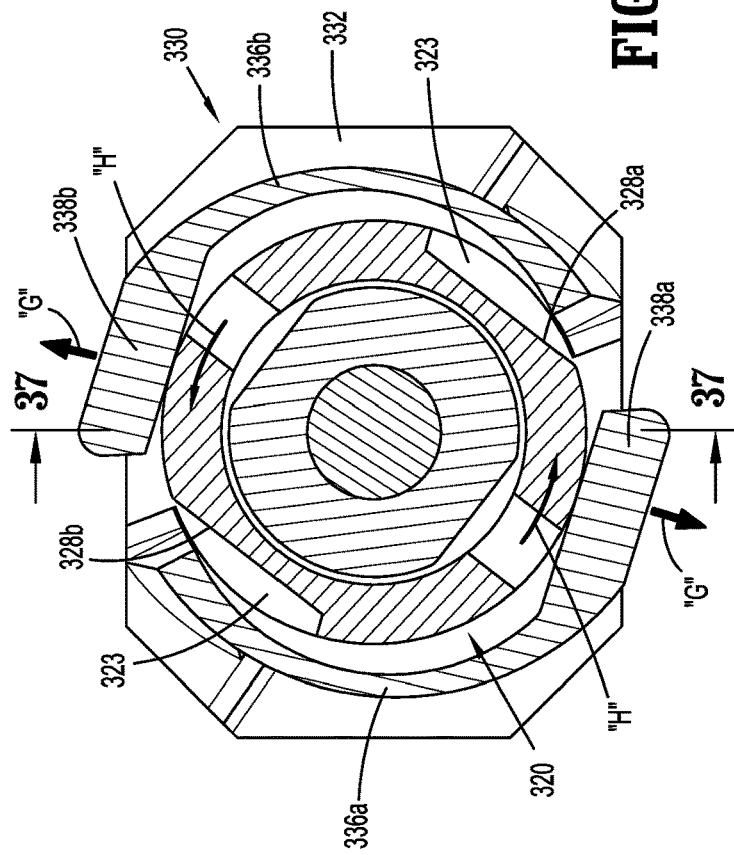
FIG. 36 is the cross-sectional side view of the trocar assembly and the retaining mechanism shown in FIG. 34, with the retaining mechanism in an unlock condition.
Figure 37:
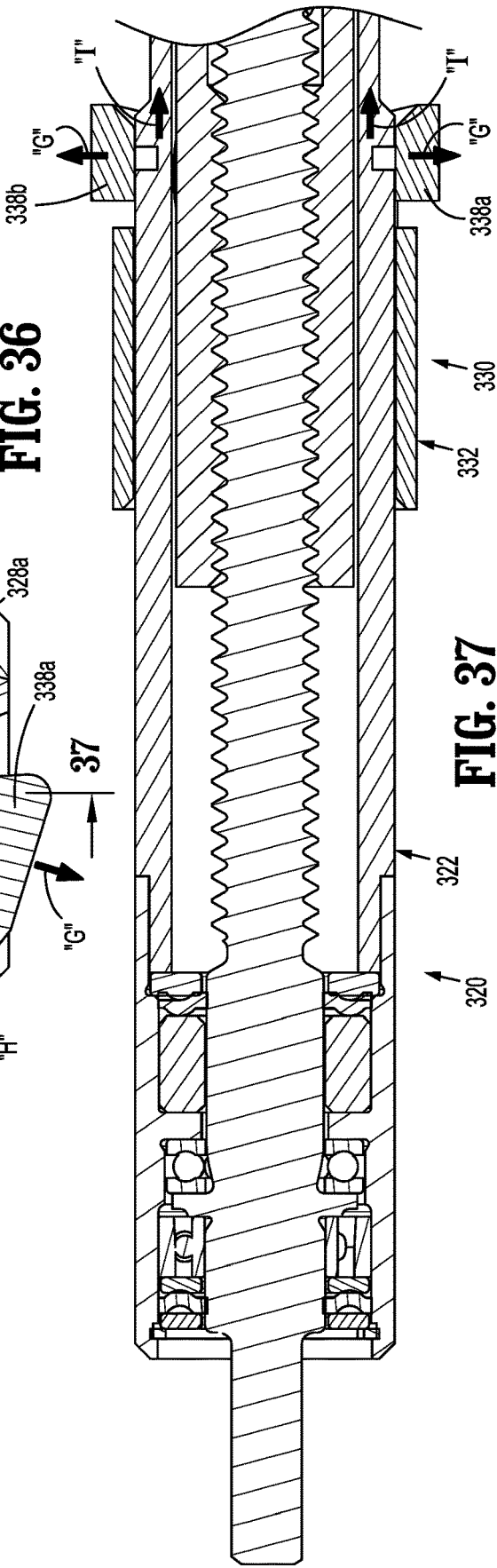
FIG. 37 is a cross-sectional side view of the trocar assembly and the retaining mechanism shown in FIGS. 30-34, taken along section line 35-35 shown in FIG. 36.
Figure 38:
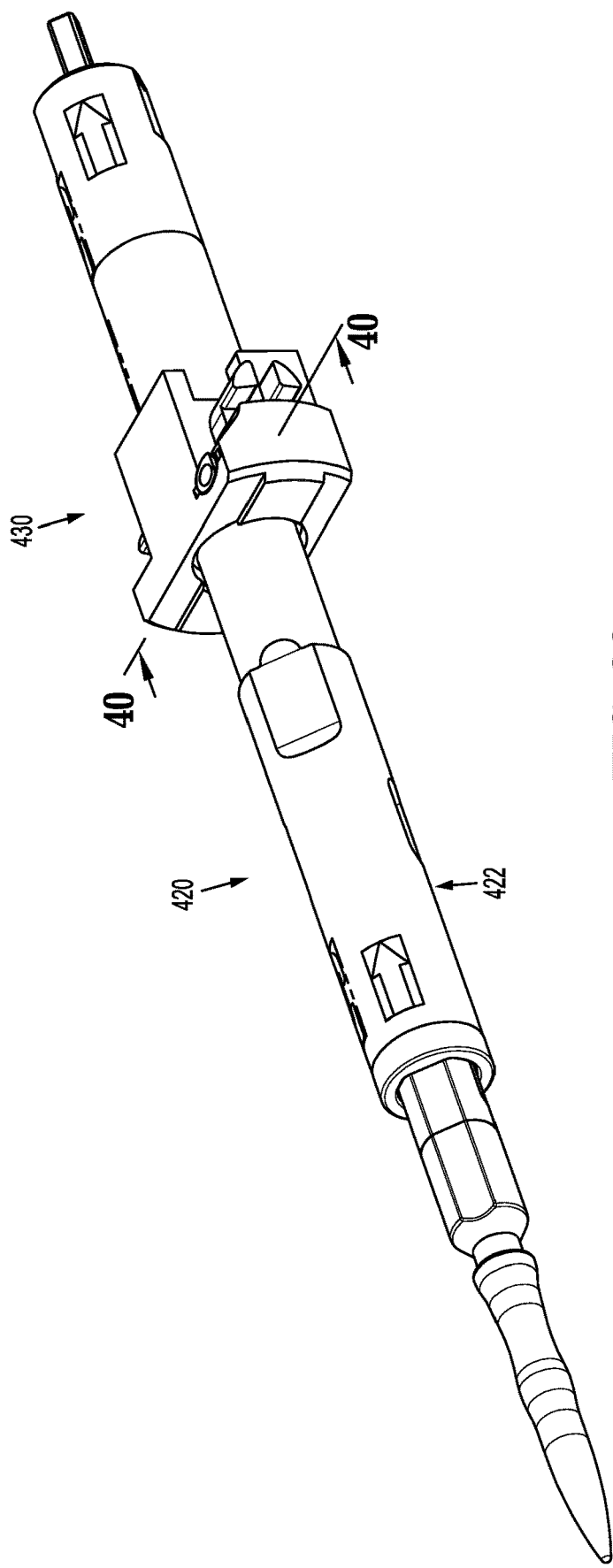
FIG. 38 is a perspective view of a trocar assembly and a retaining mechanism according to yet another exemplary embodiment of the disclosure.

FIGS. 36 and 37 illustrate the trocar assembly 320 in a second rotational orientation relative to the longitudinal axis "x" of the distal portion 304 of the adapter assembly 300, and the retaining mechanism 330 in a release configuration. In the release configuration, the lock portions 338a, 338b of first and second arms 346a, 346b of the retaining mechanism 330 are moved radially outward, as indicated by arrows "G", from within the respective first and second cutouts 323a, 323b in the trocar housing 322 of the trocar assembly 320. The lock portions 338a, 338b of first and second arms 346a, 346b move radially outward when the cam surfaces 328a, 328b defining the respective first and second cutouts 323a, 323b engage the locking portions 338a, 338b of the respective first and second arms 336a, 336b as the trocar assembly 320 is rotated about the longitudinal axis "x" of the distal portion 304 of the adapter assembly 300 to the second rotational orientation, as indicated by arrows "H" in FIG. 37.

Radial outward movement of the locking portions 338a, 338b of the first and second arms 336a, 336b, respectively, of the retaining mechanism 330 caused by the rotational movement of the trocar assembly 320 move the locking portions 338a, 338b from within the respective first and second cutouts 323a, 323b in the trocar housing 320 of the trocar assembly 320 such that the locking portions 338a, 338b no longer engage the trocar housing 322. Disengagement of the locking portions 338a, 338b from the trocar housing 322 releases the trocar assembly 320 and permits removal of the trocar assembly 320 from within the distal portion 304 of the adapter assembly 300, as indicated by arrows "I" in FIG. 37.

FIGS. 38-43 illustrate yet another exemplary aspect of the disclosure shown generally as retaining mechanism 430. The retaining mechanism 430 is substantially similar to retaining mechanism 130 described hereinabove, and will only be described in detail as relates to the differences therebetween. The retaining mechanism 430 is configured to releasably secure a trocar assembly 420 within an adapter assembly (not shown). A trocar housing 422 of the trocar assembly 420 defines first and second cutouts 423a, 423b (FIG. 40). The first and second cutouts 423a, 423b in the trocar housing 422 are at least partially defined by cam surfaces 428a, 428b.

FIG. 39 illustrates the retaining mechanism 430 including a housing 432 having a body portion 434 defining a longitudinal opening 431 for receipt of the trocar assembly 420 and first and second cylindrical opening 433a, 433b in communication with the longitudinal opening 431 in the body portion 434. The first and second cylindrical openings 433a, 433b operably receive the respective first and second retention members 440a, 440b of the retaining mechanism 430.

The first and second retention members 440a, 440b of the retaining mechanism 430 each include body 442a, 442b, respectively, having a first end portion defining a recess 443a, 443b for receiving a biasing member, e.g., compression springs 450a, 450b, respectively, and a cross opening 445a, 445b, respectively, for receiving a retaining pin 460a, 460b configured to prevent the respective first and second retention members 440a, 440b from passing entirely through the respective first and second cylindrical openings 433a, 433b. Alternatively, the first and second retention members 440a, 440b may include an annular ridge or tabs about an outer surface of the body 442a, 442b, respectively, for maintaining the respective first and second retention members 440a, 440b within first and second cylindrical openings 433a, 433b, respectively, of the body portion 434 of the housing 432 of the retaining mechanism 430. An outer sleeve 406 (FIG. 40) of the adapter assembly (not shown) maintains the compression springs 450a, 450b within the respective recesses 443a, 443b of the first and second retention members 440a, 440b, respectively.

Free ends 446a, 446b of the respective first and second retention members 440a, 440b include a cam surface 448a, 448b, respectively. The cam surfaces 448a, 448b of the respective first and second retention members 440a, 440b are configured to facilitate loading of the trocar assembly 420 within the adapter assembly (not shown). More particularly, the cam surfaces 448a, 448b face in a distal direction when secured within the housing 432 of the retaining mechanism 430 and are configured to engage a proximal portion 422a of the trocar housing 422 of the trocar assembly 420 during loading of the trocar assembly 420 with the adapter assembly (not shown). Engagement of the proximal portion 422a of the trocar housing 422 within the cam surfaces 448a, 448b causes the respective first and second retention members 440a, 440b to move radially outward, as indicated by arrow "M" in FIG. 43.

Figure 42:
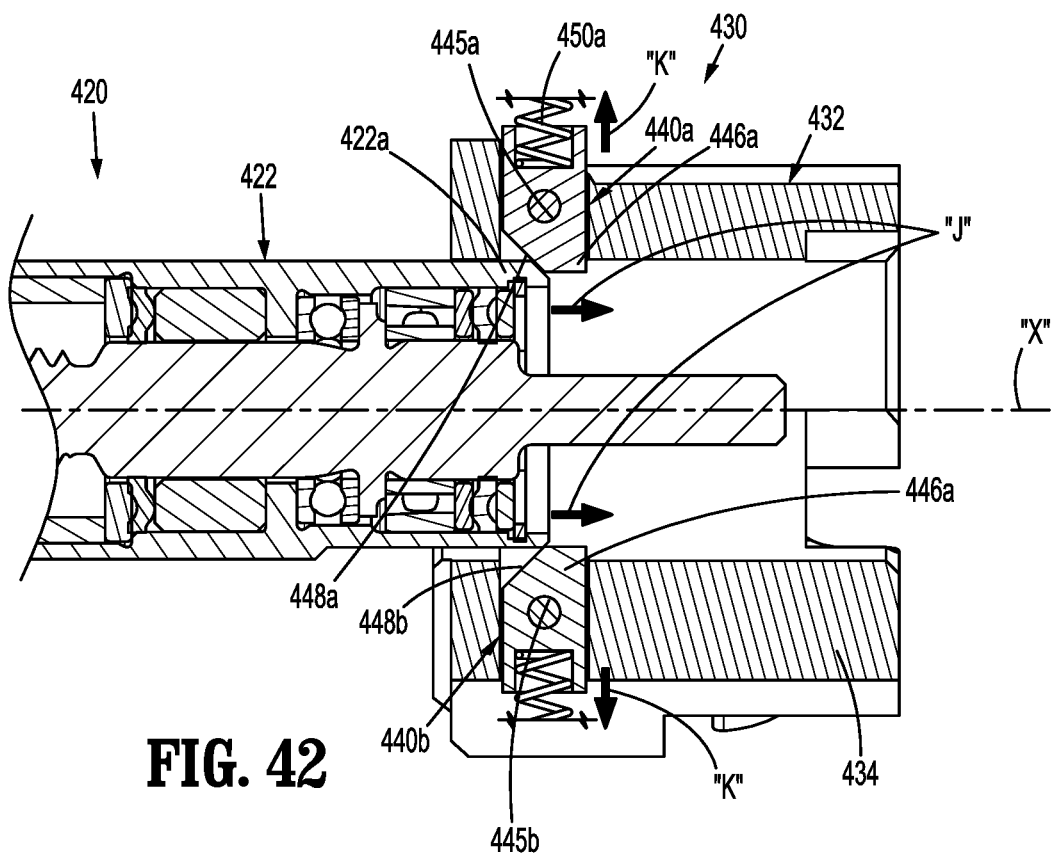
FIG. 42 is the cross-sectional view of the trocar assembly and the retaining mechanism shown in FIG. 41, with the trocar assembly partially received through the retaining mechanism.

FIG. 42 illustrates the trocar assembly 420 in a first rotational orientation as the trocar assembly 420 is received through the retaining mechanism 430, as indicated by arrows "J". More particularly, the proximal portion 422a of the trocar housing 422 of the trocar assembly 420 engages the first cam surfaces 448a, 448b of the respective first and second retention members 440a, 440b of the retaining mechanism 420. Engagement of the trocar housing 422 with the first cam surfaces 448a, 448b causes the first and second retention members 440a, 440b to move radially outward, as indicated by arrows "K". Radial outward movement of the first and second retention members 440a, 440b allows the proximal portion 422a of the trocar housing 422 of the trocar assembly 420 to be received through the housing 432 of the retaining mechanism 430.

When the first and second retention members 440a, 440b of the retaining mechanism 430 align with the first and second cutouts 423a, 423b, respectively, in the trocar housing 422 of the trocar assembly 420, the first and second compression springs 450a, 450b bias the respective first and second retention members 440a, 440b into the first and second cutouts 423a, 423b in the trocar housing 422 to secure the trocar assembly 420 within the adapter assembly (not shown). The first and second pins 460a, 460b maintain the first and second retention members 440a, 440b within the respective first and second cylindrical openings 433a, 433b in the housing 432 of the retaining mechanism 430.

Figure 43:
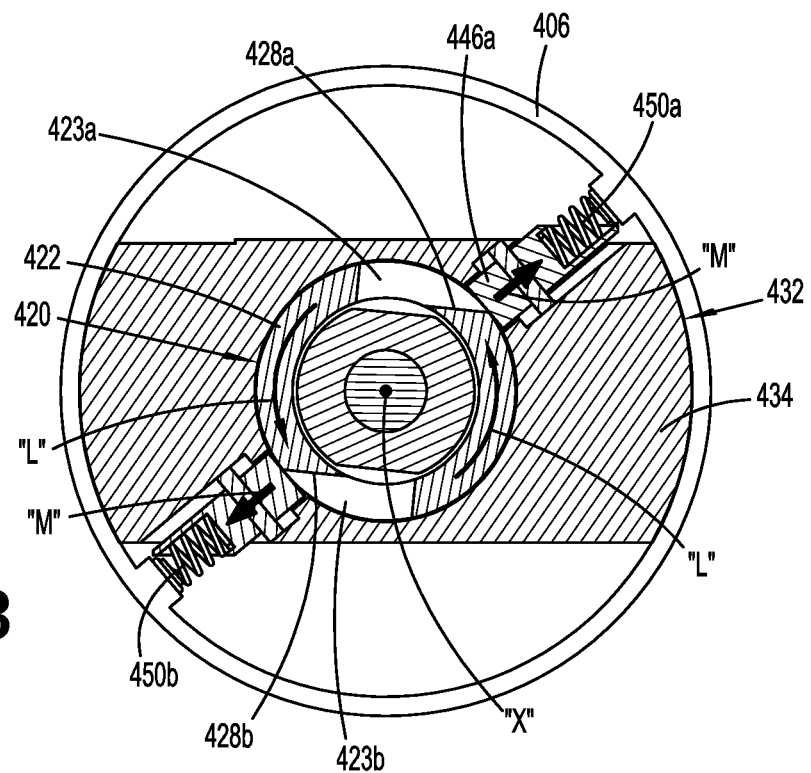
FIG. 43 is the cross-sectional end view of the trocar assembly and retaining mechanism shown in FIG. 40, with the retaining mechanism in an unlocked condition.

FIG. 43 illustrates the trocar assembly 420 in a second rotational orientation relative to the longitudinal axis "x" of the retaining mechanism 430 fully received though retaining mechanism 420 and. Rotation of the trocar assembly 420 to the second rotational orientation, as indicated by arrows "L", causes the cam surfaces 428a, 428b defining the cutouts 423a, 423b in the trocar housing 422 of the trocar assembly 420 to engage the free ends 446a, 446b of the first and second retention members 440a, 440b. Engagement of the cam surfaces 428a, 428b of the trocar housing 422 with the respective first and second retention members 440a, 440b causes the first and second retention members 440a, 440b to move radially outward, as indicated by arrows "M", to a release position.

When the first and second retention members 440a, 440b of the retaining mechanism 430 are in the release position, the trocar assembly 420 may be withdrawn from the longitudinal passage 431 through the housing 432 in the retaining mechanism 430 to permit separation of the trocar assembly 420 from the adapter assembly (not shown).

FIGS. 44-49 illustrate another aspect of an adapter assembly including a trocar assembly 520 and a retaining mechanism 530 according to another exemplary aspect of the disclosure for releasably retaining the trocar assembly 520 within the adapter assembly 500.

FIG. 45 illustrates the retaining mechanism 530 disposed within a distal portion 504 of the elongate body of the adapter assembly 500. A seal member 508 is disposed proximal of the retaining mechanism 530. The seal member 508 is formed of an elastomeric material and is configured to be frictionally engaged by first and second retention members 540a, 540b of the retaining mechanism 530 to retain the first and second retention members 540a, 540b in a locked position (FIG. 49).

Figure 46:
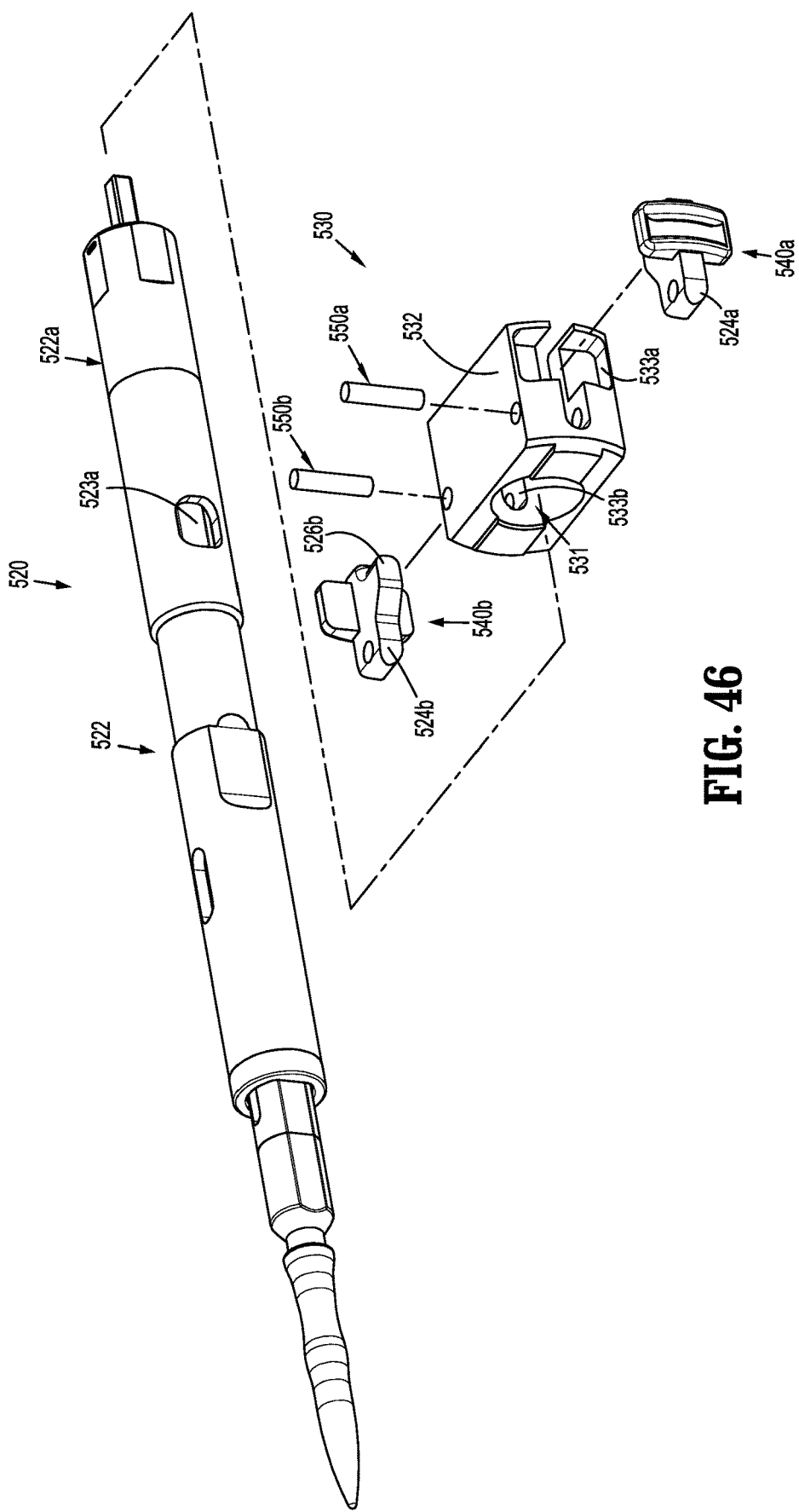
FIG. 46 is a perspective view of the trocar assembly and the retaining mechanism shown in FIG. 45, with components of the retaining mechanism separated.
Figure 47:
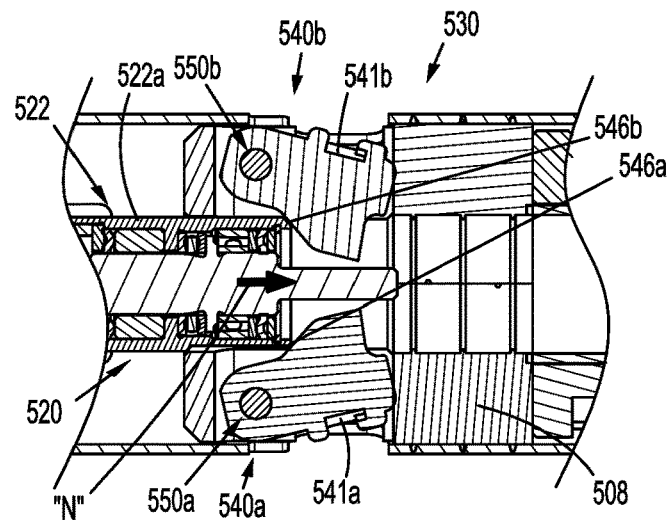
FIG. 47 is a cross-sectional top view of a portion of the adapter assembly including the retaining mechanism, with a proximal portion of the trocar assembly in initial engagement with locking members of the retaining mechanism.
Figure 48:
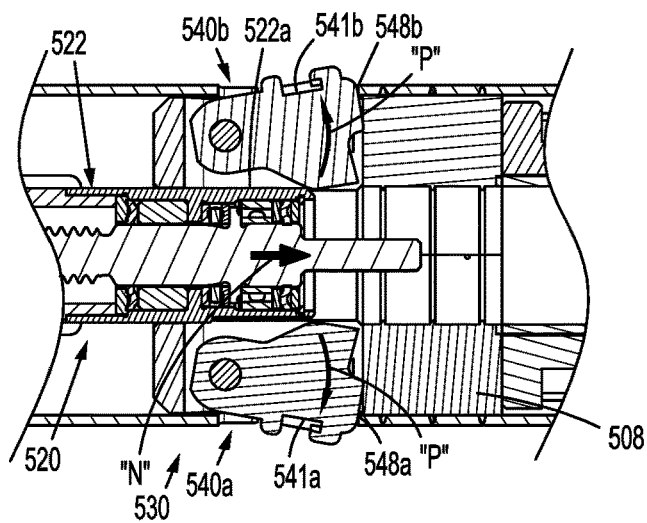
FIG. 48 is the cross-sectional top view of the portion of the adapter assembly including the retaining mechanism shown in FIG. 47, with the proximal portion of the trocar assembly partially received through the retaining mechanism.

FIG. 46 shows the trocar housing 522 of the trocar assembly 520 defining first and second openings 523a, 523b, and the retaining mechanism 530 including a housing 532 and the first and second retention members 540a, 540b. The housing 532 of the retaining mechanism 530 defines a longitudinal passage 531 for receipt of a proximal portion 522a of the trocar housing 522 of the trocar assembly 520, and first and second recesses 533a, 533b in fluid communication with the longitudinal passage 531 for operably receiving the respective first and second retention members 540a, 540b. The first and second retention members 540a, 540b are pivotally secured within the respective first and second recesses 533a, 533b of the housing 532 by a pivot pin 550a, 550b.

Each of the first and second retention members 540a, 540b includes a body 542a, 542b, respectively, having a camming surface 544a, 544b, respectively, a locking surface 546a, 546b, and an engagement surface 548a, 548b. The camming surfaces 544a, 544b of the respective first and second retention members 540a, 540b are configured to be engaged by the proximal portion 522a of the trocar housing 522 of the trocar assembly 520 during loading of the trocar assembly 520 within the adapter assembly 500, as indicated by arrow "N" in FIGS. 47 and 48, to pivot the first and second retention members 540a, 540b from an initial or preloading position to a loading or release position, as indicated by arrows "P" in FIG. 48, to permit receipt of the proximal portion 522a of the trocar housing 522 through the housing 532 of the retaining mechanism 530. The locking surfaces 546a, 546b of the respective first and second retention members 540a, 540b are configured to engage the trocar housing 522 of the trocar assembly 520 when the first and second retention members 540a, 540b are in their locked positions (FIG. 49). The engagement surfaces 548a, 548b of the respective first and second retention members 540a, 540b are configured to frictionally engage the seal member 508 of the adapter assembly 500 to maintain the first and second retention members 540a, 540b in their locked positions. The body portions 542a, 542b of the respective first and second retention members 540a, 540b may be configured to facilitate engagement of the first and second retention members 540a, 540b by a user. In certain aspects of the disclosure, and as shown, the body portions 542a, 542b of the respective first and second retention members 540a, 540b define slots 541a, 541b, respectively, configured for engagement by fingernails of a user.

Figure 49:
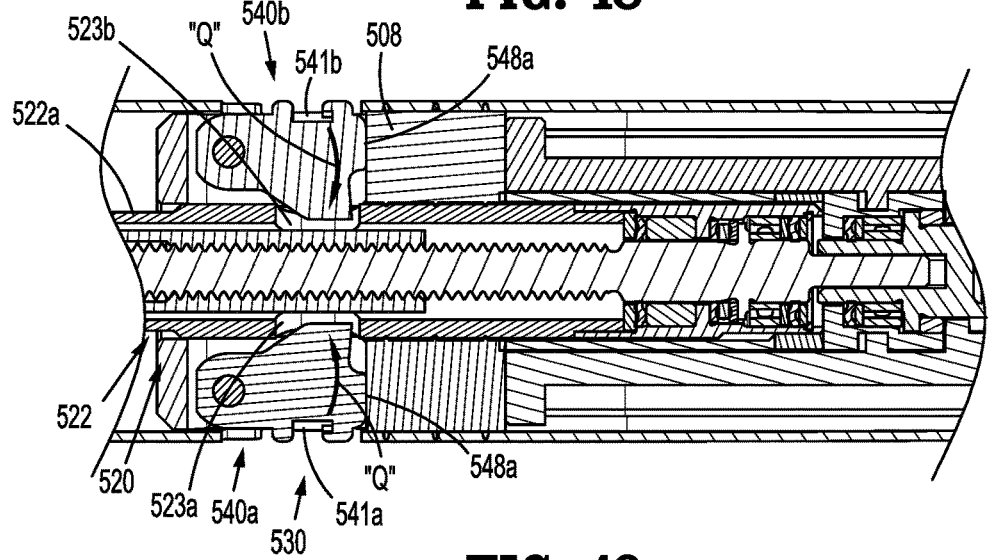
FIG. 49 is the cross-sectional top view of the portion of the adapter assembly including the retaining mechanism shown in FIG. 47, with the proximal portion of the trocar assembly fully received through the retaining mechanism.
Figure 50:
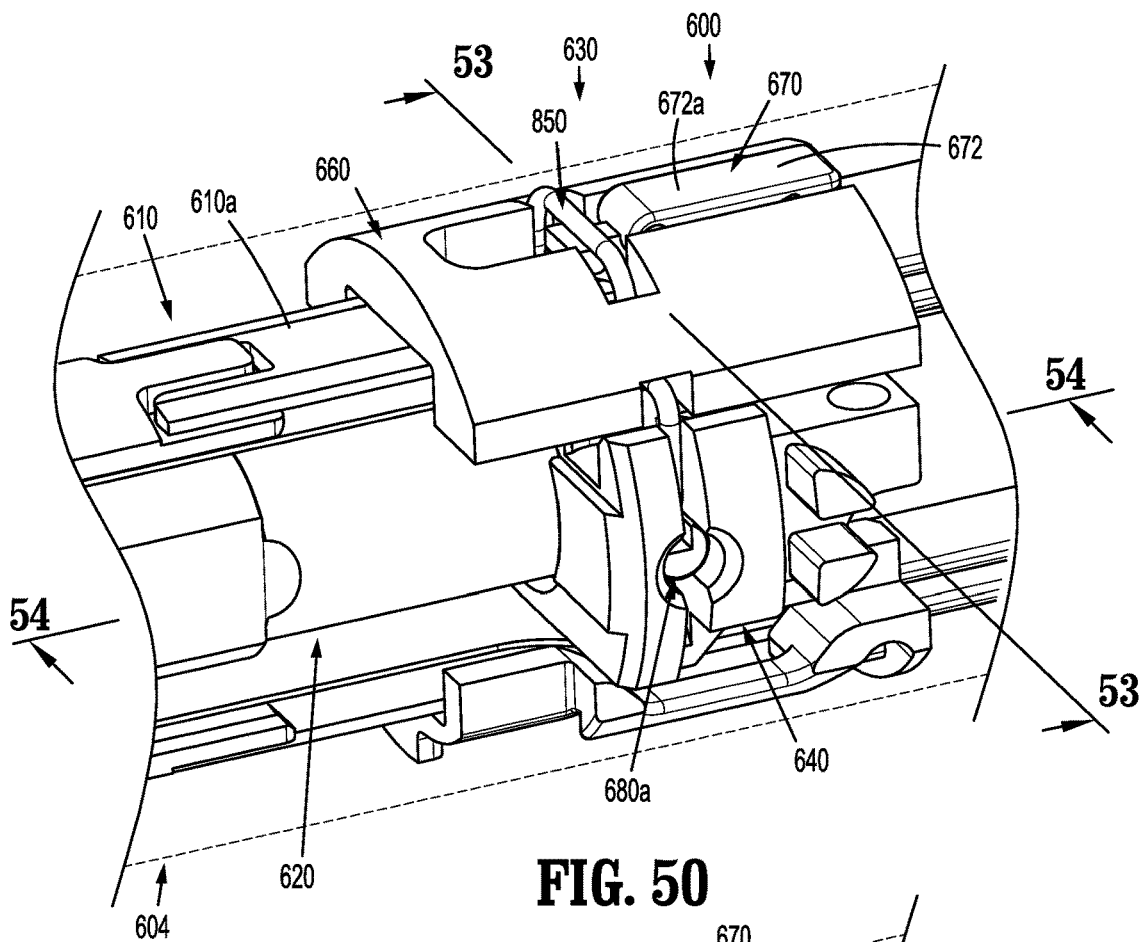
FIG. 50 is a side perspective sectional view of an adapter assembly according to still yet another exemplary embodiment of the disclosure including a retaining mechanism and a trocar assembly fully received through the retaining mechanism.
Figure 51:
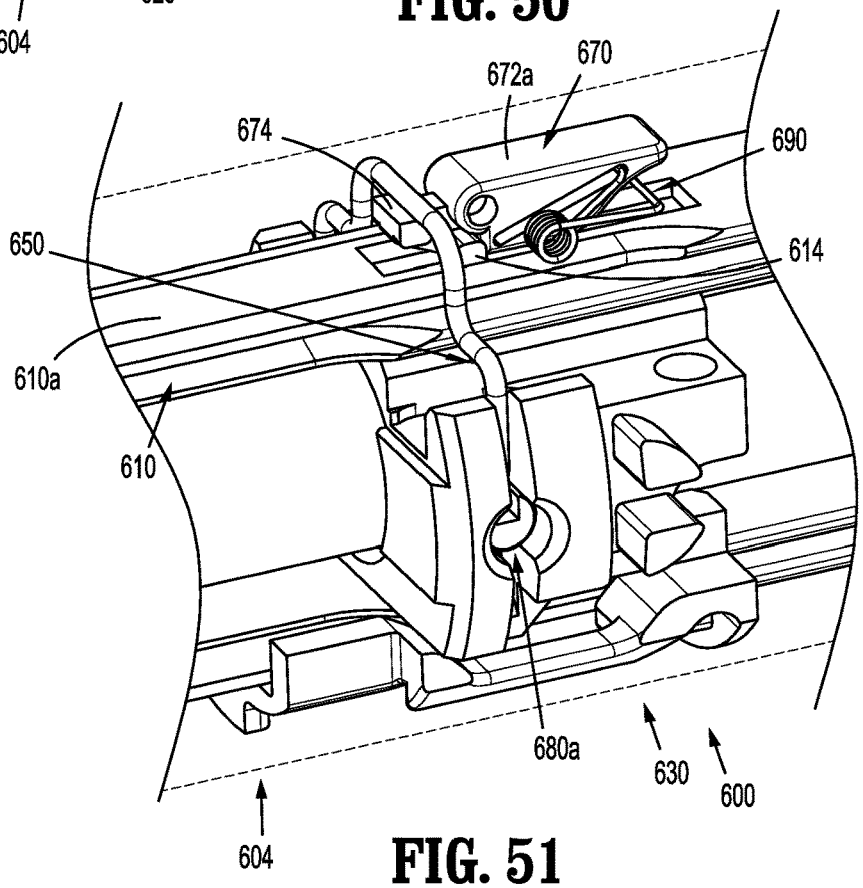
FIG. 51 is the side perspective sectional view of the trocar assembly and retaining mechanism shown in FIG. 50, with a housing of the retaining mechanism removed.

FIG. 49 illustrates the trocar assembly 520 fully received within the distal portion 504 of the adapter assembly 500 and the first and second retention members 540a, 540b in the locked position. The first and second retention members 540a, 540b move to the locked position by pivoting of the first and second retention members 540a, 540b radially inwardly, as indicated by arrows "Q". As the first and second retention members 540a, 540b pivot to the locked position, the locking surfaces 546a, 546b of the respective first and second retention members 540a, 540b engage the trocar housing 522 to secure the trocar assembly 520 within the adapter assembly 500.

Removal the trocar assembly 520 from within the adapter assembly 500 includes pivoting the first and second retention members 540a, 540b of the retaining mechanism 540 radially outward to disengage the locking surfaces 546a, 546b of the respective first and second retention members 540a, 540b from the trocar housing 522 of the trocar assembly 520. It is envisioned that the first and second retention members 540a, 540b may be moved to the release position directly through engagement by a user, and/or with the assistance of a removal tool (not shown). In some aspects, the retaining mechanism 530 may include biasing members (not shown) for biasing the first and second retention members 540a, 540b to the locked position.

FIGS. 50-57 illustrate yet another adapter assembly 600 including a trocar assembly 620, and a retaining mechanism 630 according to another exemplary aspect of the disclosure releasably securing the trocar assembly 620 relative to an outer sleeve (not shown) of the adapter assembly 600.

The trocar assembly 620 of the adapter assembly 600 includes a trocar housing 622 defining first and second locking openings 623a, 623b (FIG. 53) for receiving respective first and second retainer members 680a, 680b of the retaining mechanism 630 of the adapter assembly 600. The retaining mechanism 630 includes a retaining block 640, a cam wire 650 supported by the retaining block 640, a retaining block extension 660 for maintaining the cam wire 650 relative to the retaining block 640, a button member 670 in operable engagement with the cam wire 650 and pivotally supported relative to the retaining block 640, and first and second retainer members 680a, 680b (FIG. 52) supported by the cam wire 650 within the retaining block 640. A torsion spring 690 biases the button member 670 to a first, locked position (FIG. 54).

Figure 55:
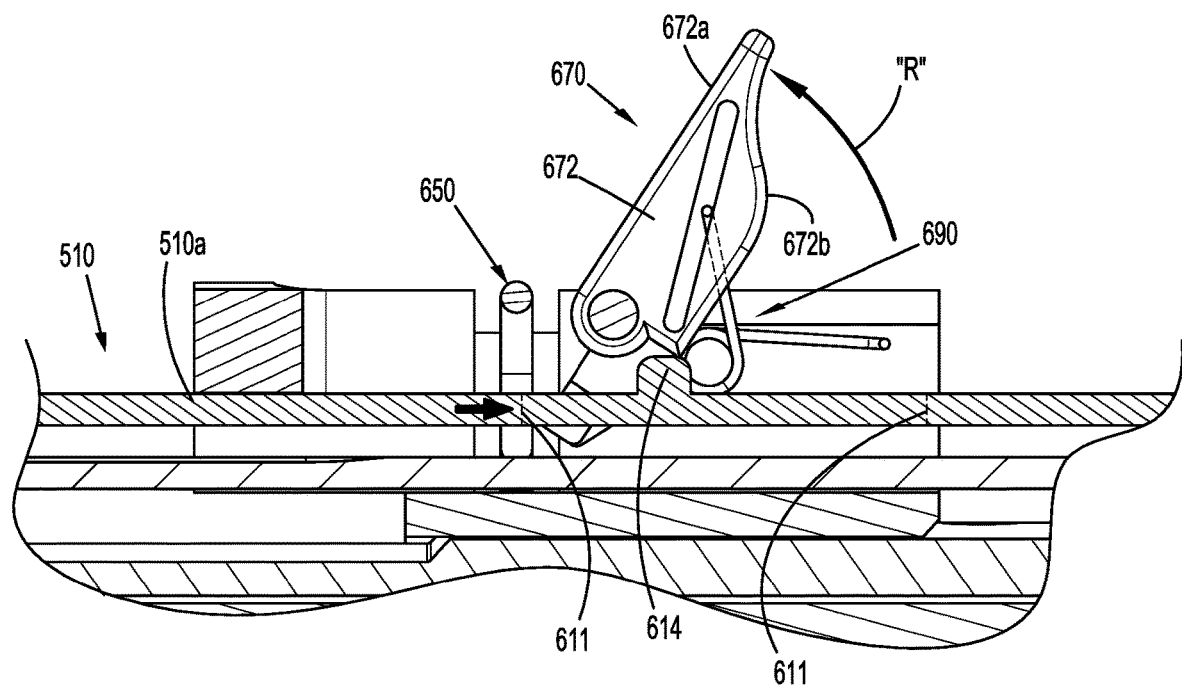
FIG. 55 is the cross-sectional side cutaway view of the adapter assembly shown in FIG. 54, with the retaining mechanism in a partially locked configuration.
Figure 56:
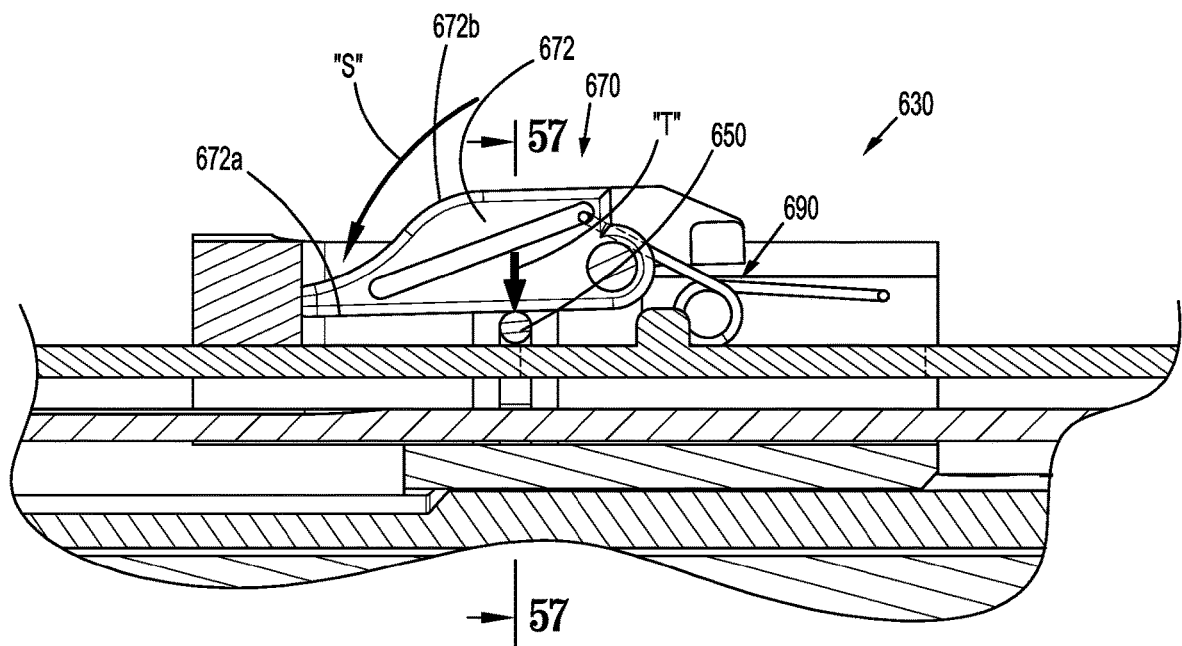
FIG. 56 is the cross-sectional side cutaway view of the adapter assembly shown in FIGS. 54 and 55, with the retaining mechanism in an unlocked configuration.

A first drive member 610a of a first drive assembly 610 extends through the retaining mechanism 630 of the adapter assembly 600 through the cam wire 650 and between the retaining block 640 and the retaining block extension 660. The first drive member 610a includes a stop feature 614 and defines a cutout 611 configured to accommodate pivoting of the button member 670. During operation of the adapter assembly 600, the first drive member 610a is moveable from a first, distal position (FIG. 54) to subsequent proximal positions (FIGS. 55 and 56) to cause the movement of the button member 670 from the locked position (FIG. 54), to a partially locked position (FIG. 55), to a release position (FIG. 56).

Figure 52:
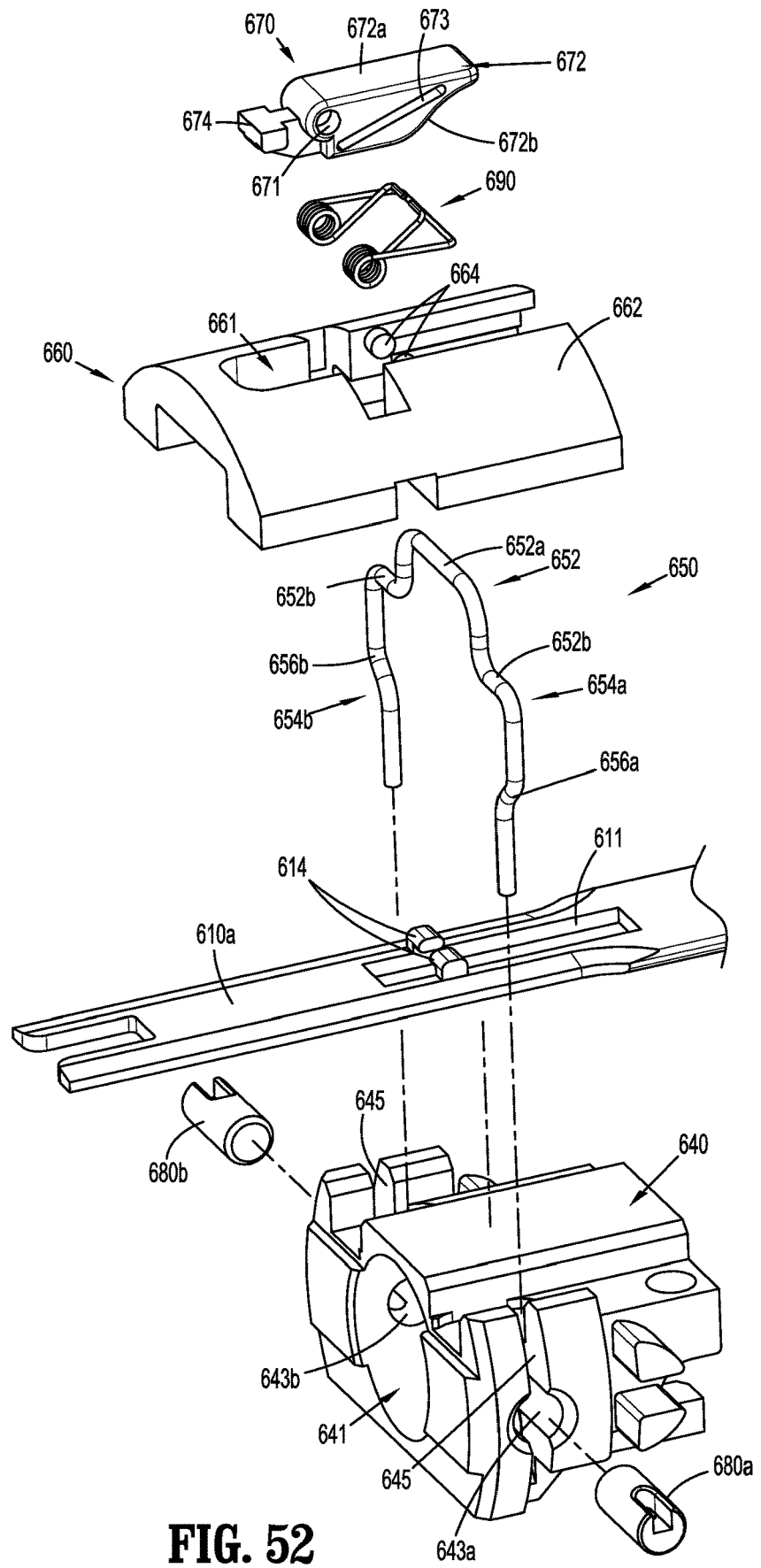
FIG. 52 is a side perspective view of the retaining mechanism shown in FIGS. 50 and 51, with components separated, and including a distal end of a drive member.

FIG. 52 illustrates the retaining block 640 of the retaining mechanism 630 defining a longitudinal passage 641 for receiving the trocar assembly 620 (FIG. 53), first and second opposed cylindrical openings 643a, 643b in communication with the longitudinal passage 641 for receiving the respective first and second retainer members 680a, 680b, and a channel or slot 645 extending about a perimeter of the retaining block 640 and through the first and second cylindrical openings 643a, 643b in the retaining block 640 for receiving the cam wire 650. The first and second retainer members 680a, 680b of the retaining mechanism 630 are supported within the first and second cylindrical openings 643a, 643b of the retaining block 640 by the cam wire 650 and are configured to be received within first and second locking openings 623a, 623b (FIG. 53) of the trocar housing 622 of the trocar assembly 620 when the trocar assembly 620 is fully received within the distal portion 604 of the adapter assembly 600.

The cam wire 650 of the retaining mechanism 630 includes a substantially U-shaped member having a backspan 652, and first and second legs 654a, 654b extending from the backspan 652. The backspan 652 includes a button engagement portion 652a and a pair of shoulders portions 652b on either side of the button engagement portion 652a. Each of the first and second legs 654a, 654b includes an opposed angled section 656a, 656b. The cam wire 650 is received within the channel 645 of the retaining block 640. The cam wire 650 is moveable between a lock position (FIG. 53) when the button member 870 is in the locked position, and a release position when the button member 670 is pivoted through the partially locked position (FIG. 54) to the release position (FIG. 55).

The retaining block extension 660 includes a frame 662 defining an opening 661 and having a pair of pivot members 664 extending within the opening 661. The button member 670 is pivotally supported within the opening 661 in the frame 662 by the pivot members 664.

The button member 670 of the retaining mechanism 630 includes a body portion 672 having a first engagement surface 672a, and a second engagement surface 672b, each of which is configured for operable engagement by a user. A flange 674 extends from the body portion 672 of the button member 670 and is configured to engage the stop feature 614 on the first drive member 610a of the first drive assembly 610 when the first drive member 610a is in the distal position. The body portion 672 of the button member 670 defines a cylindrical opening 671 for receiving the pivot members 664 of the retaining block extension 660, and a slot 673 for receiving a portion of the torsion spring 690.

The first engagement surface 672a of the body portion 672 of the button member 670 of the retaining mechanism 630 is configured to engage the engagement portion 652a of the backspan 652 of the cam wire 650.

The first and second retention members 680a, 680b of the retaining mechanism 630 form substantially cylindrical bodies 682a, 682b and are supported on the angled portions 656a, 656b of the respective first and second legs 654a, 654b of the cam wire 650. The first and second retention members 680a, 680b may include tapered inner surfaces 682a, 682b to facilitate receipt of the trocar assembly 620 through the retaining block 640 of the retaining mechanism 630.

The first and second retention members 680a, 680b each define a stepped opening 681a, 681b through which the respective angled portion 656a, 656b of the cam wire 650 is received. The cam wire 650 and the stepped openings 681a, 681b of the respective first and second retention members 680a, 680b are configured such that when the cam wire 650 is in the first position, the first and second retention members 680a, 680b extend from within the retaining block 640 into the longitudinal passage 641. In this manner, when a trocar assembly 620 is fully received within the distal portion 604 of the adapter assembly 600, the first and second retention members 680a, 680b are received within the respective first and second locking openings 623a, 623b of the trocar housing 622 of the trocar assembly 620. Conversely, when the cam wire 650 is in the second or release position, the first and second retention members 680a, 680b are retracted from within the longitudinal passage 641 of the retaining block 640 to permit insertion and/or removal of the trocar assembly 620 from the distal portion 604 of the adapter assembly 600.

Figure 53:
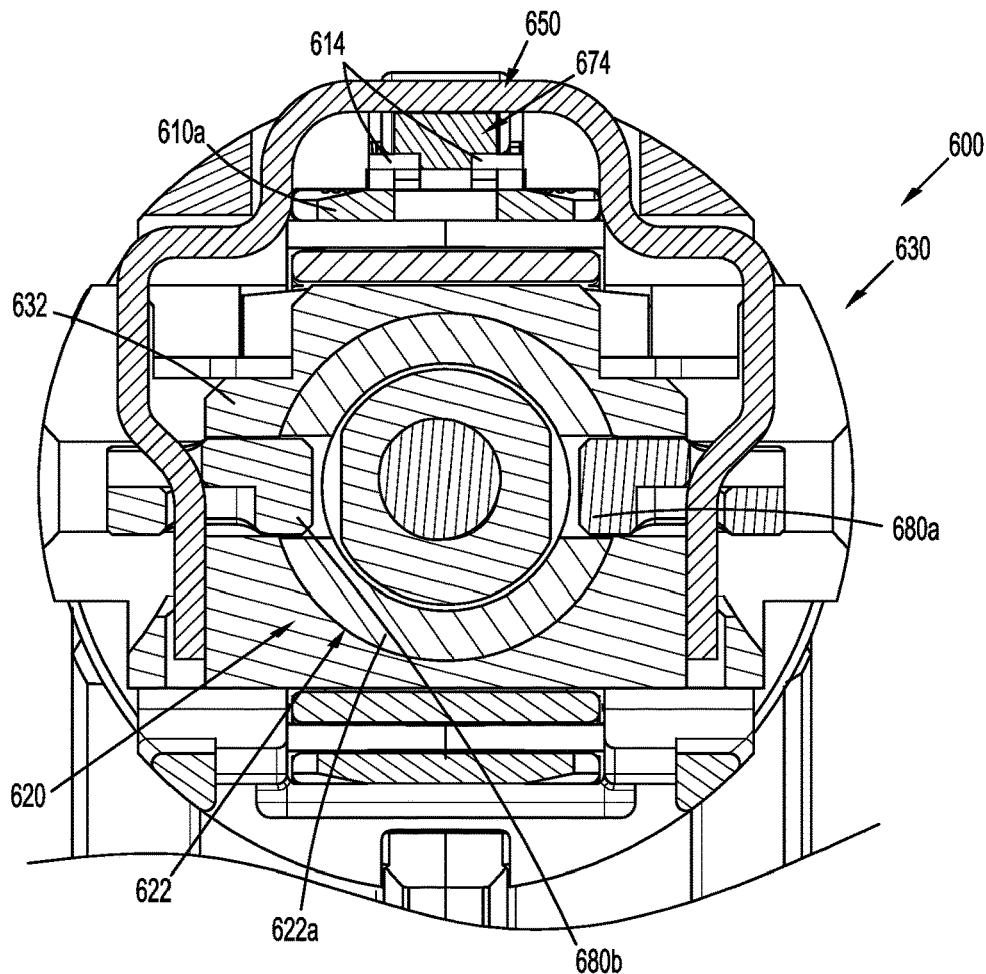
FIG. 53 is a cross-sectional end view taken along section line 53-53 shown in FIG. 50, with the retaining mechanism in a locked configuration.
Figure 54:
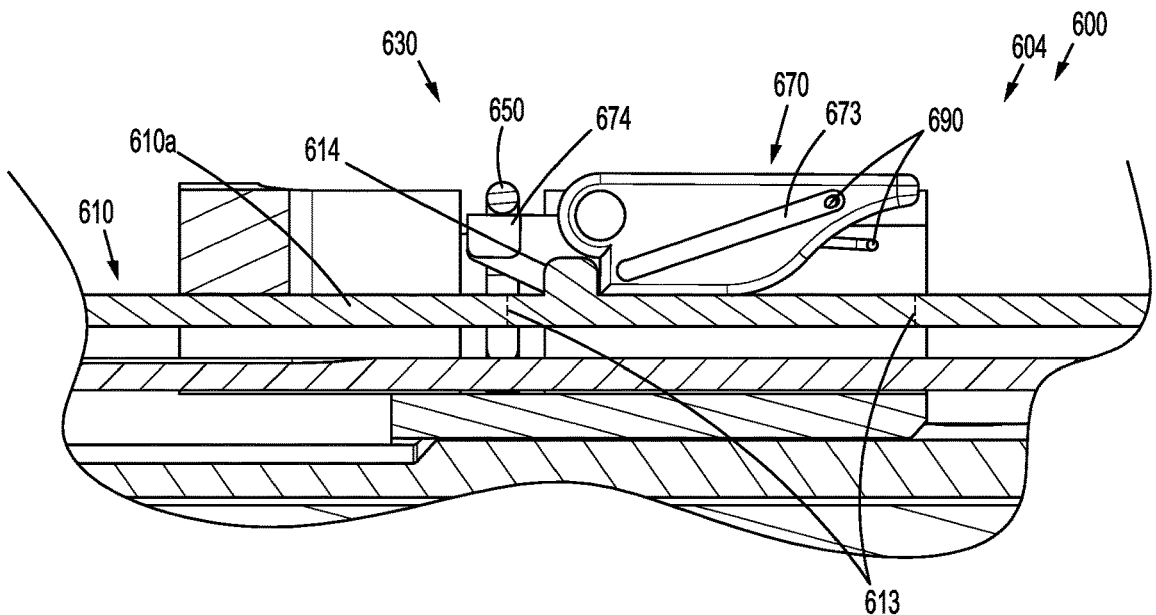
FIG. 54 is a cross-sectional side cutaway view of the adapter assembly shown in FIG. 50, taken along section line 54-54 shown in FIG. 50, with the retaining mechanism in the locked configuration.

FIGS. 53 and 54 illustrate the retaining mechanism 630 of the adapter assembly 600 with the cam wire 650 in the lock position, and the button member 670 in the locked position. The trocar assembly 620 is securely received within the distal portion 604 of the adapter assembly 600. The cam wire 650 of the retaining mechanism 630 is secured in the lock position by the flange 674 of the button member 670.

FIG. 55 illustrates the button member 670 of the retaining mechanism 630 in the partially locked position. Proximal movement of the first drive member 610a of the first drive assembly 610, as indicated by arrow "R", engages the stop feature 614 of the first drive member 610a with the body portion 672 of the button member 670 to cause pivoting of the of the button member 670 in a first direction, as indicated by arrow "S". Pivoting of the button member 670 to the partially locked position exposes the second engagement surface 672b of the button member 670 to permit engagement of the second engagement surface 672b by the user.

Figure 57:
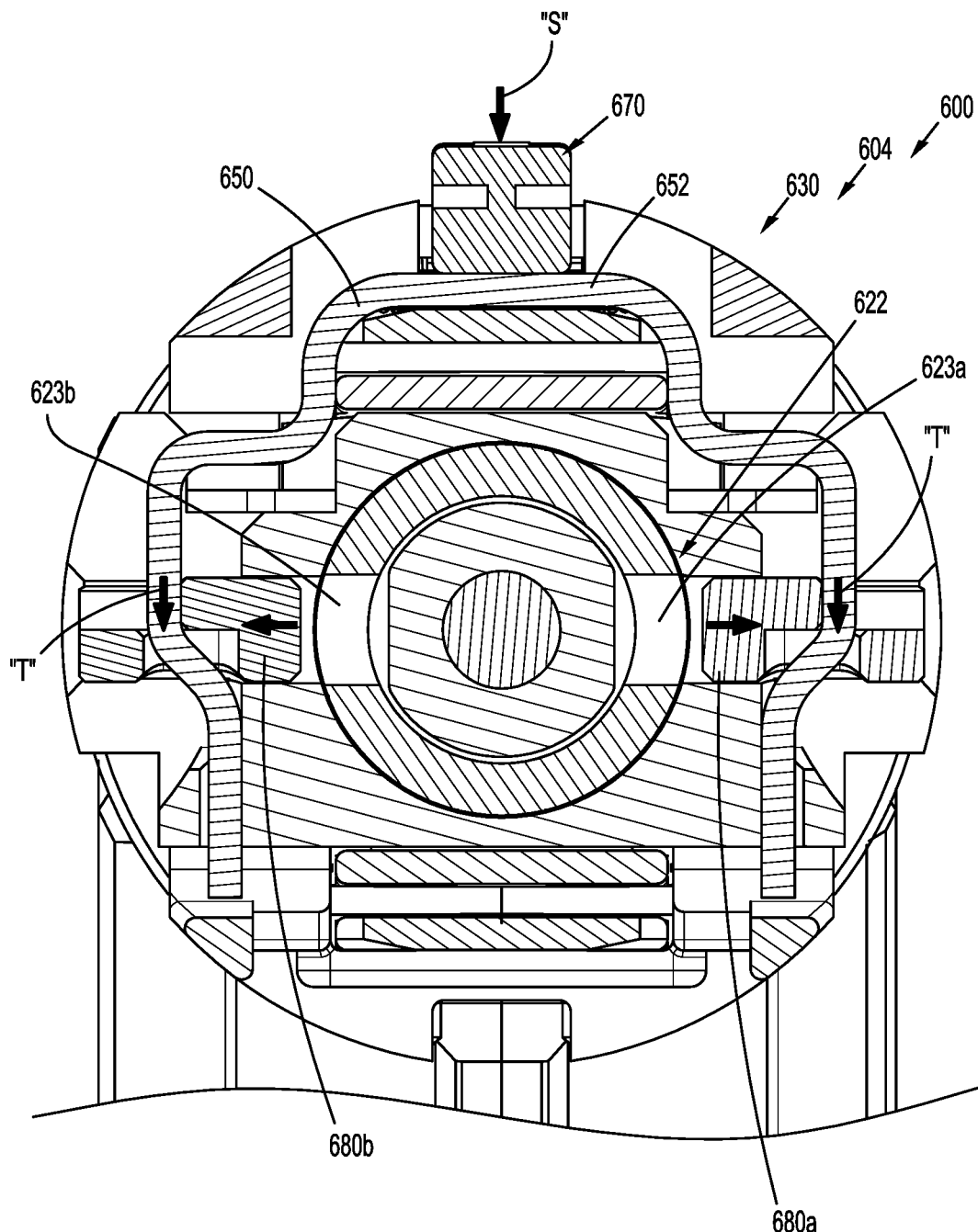
FIG. 57 is the cross-sectional end view of the adapter assembly shown in FIG. 53, with the retaining mechanism in the unlocked configuration.
Figure 58:
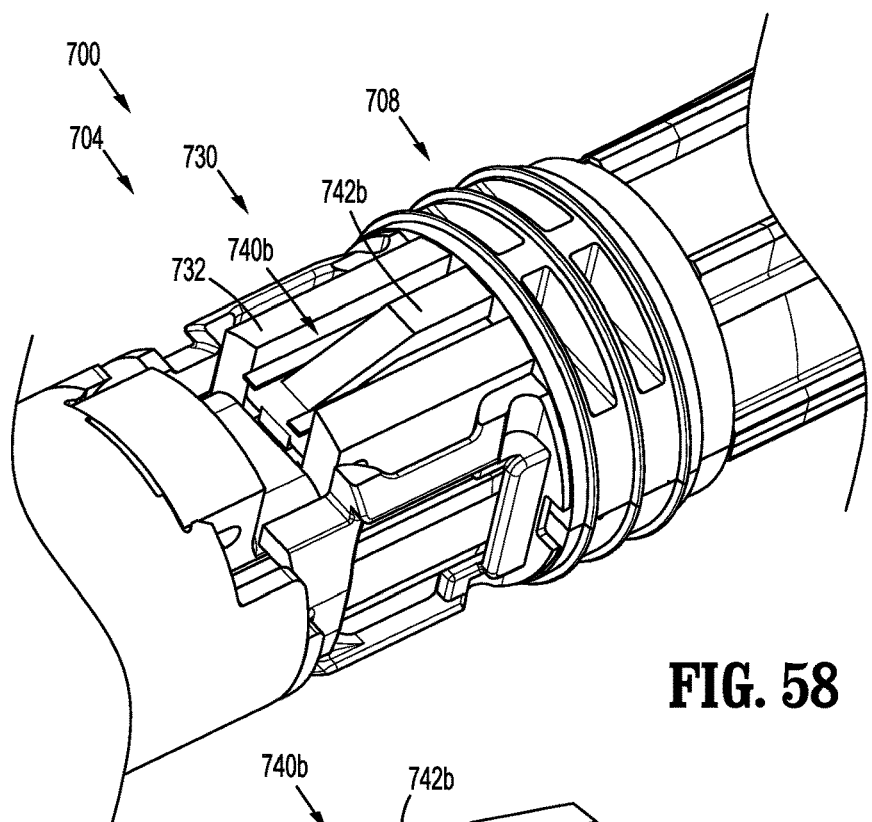
FIG. 58 is a perspective top view of an adapter assembly according to still another exemplary embodiment of the disclosure, including a retaining mechanism for releasably receiving a trocar assembly.

FIGS. 56 and 57 illustrate the button member 670 of the retaining assembly 630 in the release position. To move the button member 670 to the release position, the user (not shown) continues to pivot the button member 670 in the first direction, as indicated by arrow "S", to cause the first engagement surface 672a of the button member 670 to engage the engagement portion 652 of the cam wire 650. Engagement of the cam wire 650 by the button member 670 causes the cam wire 650 to move to the release position, as indicated by arrows "T" in FIG. 57. Movement of the cam wire 650 to the release position causes the first and second retention members 680a, 680b to move radially outward, out of engagement with the trocar housing 622 of the trocar assembly 620.

Once the first and second retention members 680a, 680b of the retaining mechanism 630 are disengaged from the trocar housing 622 of the trocar assembly 620, the trocar assembly 620 may be removed from within the distal portion 604 of the adapter assembly 600.

FIGS. 58-62 illustrate an adapter assembly 700 including a retaining mechanism 730 according to still yet another aspect of the disclosure for releasably securing a trocar assembly 730 within a distal portion 704 of the adapter assembly 700. The retaining mechanism 730 is substantially similar to the retaining mechanism 530 described hereinabove, and will only be described in detail as relates to the differences therebetween.

Figure 59:
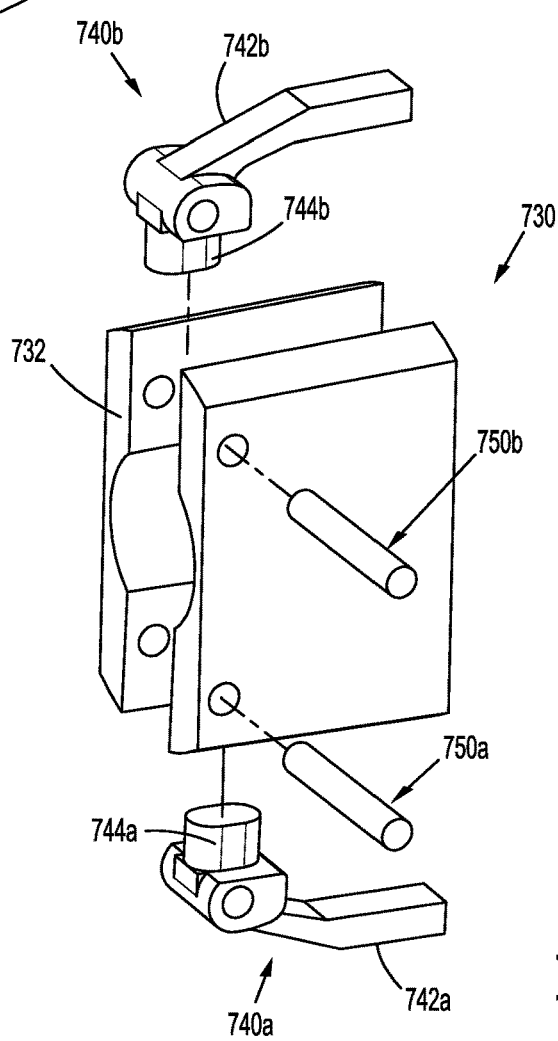
FIG. 59 is a perspective side view of the retaining mechanism shown in FIG. 58, with components separated.

FIG. 59 shows the retaining mechanism 730 including a housing 732 supporting first and second retention members 740a, 740b. The first and second retention members 740a, 740b are pivotally supported by pivot pins 750a, 750b, respectively, and are pivotable between a locked position (FIG. 60), a partially released position (FIG. 61), and a release position (FIG. 62).

The first and second retention members 740a, 740b each include a handle portion 742a, 742b and a locking portion 744a, 744b. The handle portions 742a, 742b of the respective first and second retention members 740a, 740b are configured for operable engagement by a user. Free ends 746a, 746b of the respective handle portions 742a, 742b are positioned and configured to frictionally engage a seal member 708 of the adapter assembly 700 to maintain the respective first and second retention members 740a, 740b in a locked position.

Figure 60:
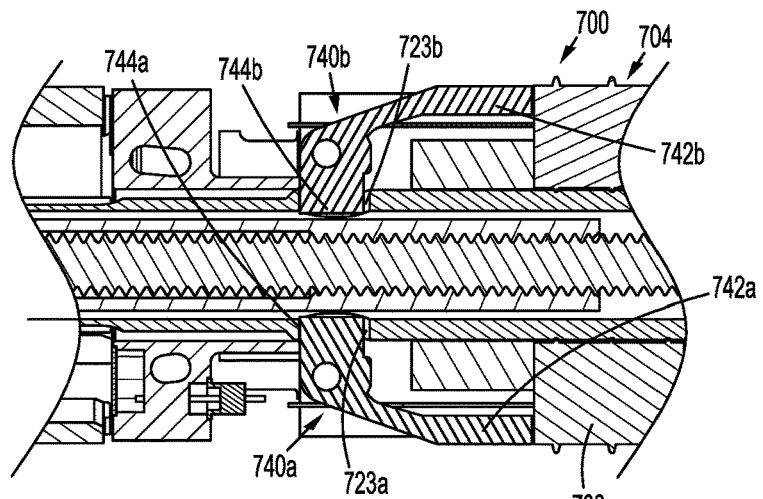
FIG. 60 is a cross-sectional side view of the adapter assembly shown in FIG. 58, with the retaining mechanism in a locked configuration.

FIG. 60 illustrates the first and second retention members 740a, 740b in the locked position. In the locked position, the locking portion 744a, 744b of the respective first and second retention members 740a, 740b of the retaining mechanism 730 are received within first and second openings 723a, 723b of a trocar housing 722 of the trocar assembly 720. In the locked position, the handle portions 742a, 742b of the respective first and second retention members 740a, 740b frictionally engage the seal member 708 of the adapter assembly 700 to [maintain the respective first and second retention members 740a, 740b in the locked position.

Figure 61:
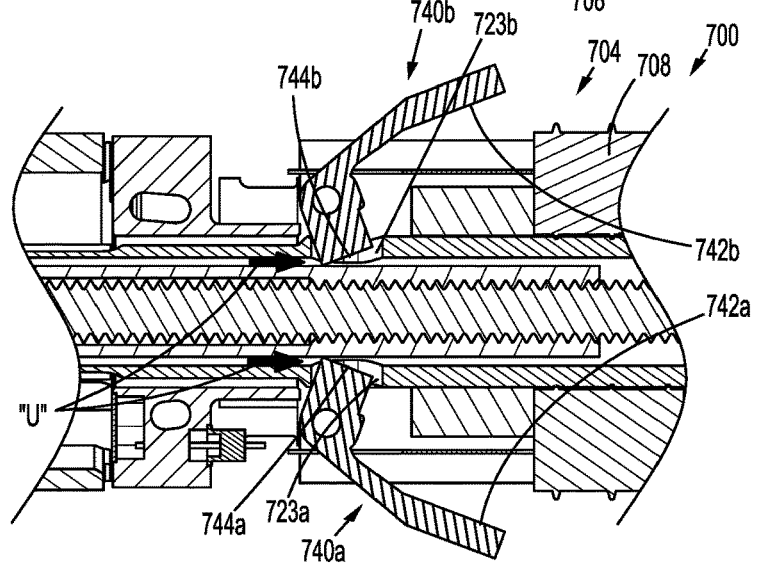
FIG. 61 is the cross-sectional side view of the adapter assembly shown in FIG. 60, with the retaining mechanism in a partially locked configuration.
Figure 62:
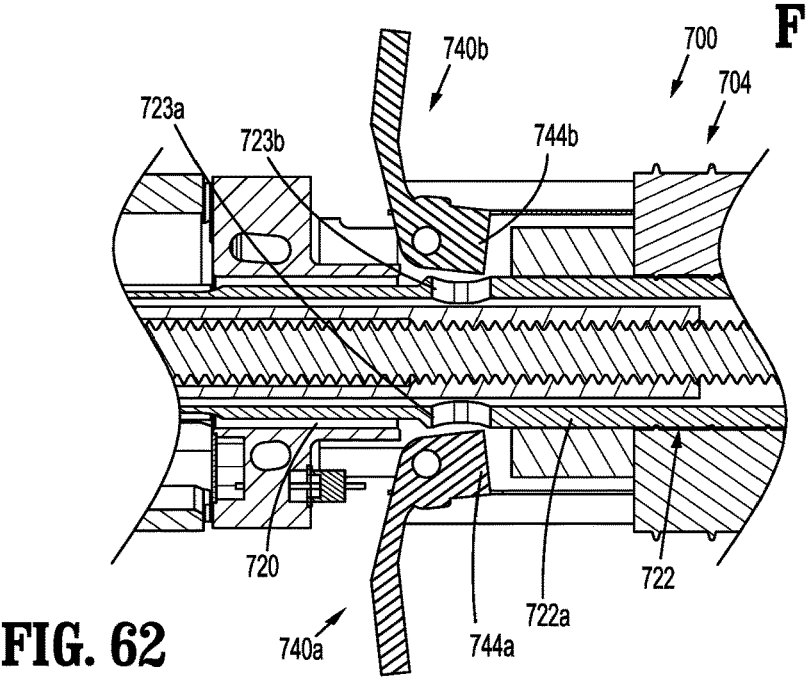
FIG. 62 is the cross-sectional side view of the adapter assembly shown in FIGS. 60 and 61, with the retaining mechanism in an unlocked configuration.

FIG. 61 shows proximal movement of the trocar assembly 730 as indicated by the arrow "U". During proximal movement of the trocar assembly 730, engagement of the trocar housing 722 of the trocar assembly 720 with the locking portions 744a, 744b of the respective first and second retention members 740a, 740b causes the first and second retention members 740a, 740b to pivot to the partially locked position. In the partially locked position, the handle portions 742a, 742b of the respective first and second retention members 740a, 740b are engageable by a user to continue pivoting the first and second retention members 740a, 740b to the release position.

FIG. 62 illustrates the first and second retention members 740a, 740b of the retaining mechanism 730 in the release position. When in the release position, the locking portions 744a, 744b of the respective first and second retention members 740a, 740b are completely retracted from within the first and second openings 723a, 723b, respectively, in the trocar housing 722 of the trocar assembly 720. In this manner, the trocar assembly 720 may be removed from within the distal portion 704 of the adapter assembly 700.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described.

What is claimed is:

1. An adapter assembly for connecting a loading unit to a handle assembly, the adapter assembly comprising:
    an elongate body having a proximal portion and a distal portion, the proximal portion being configured for operably engagement with an actuation assembly and the distal portion defining a longitudinal axis and being configured to operably receive a trocar assembly; and
    a seal member disposed within the distal portion of the elongate body; and
    a retaining mechanism disposed adjacent the seal member and configured to releasably secure the trocar assembly within the distal portion of the elongate body, the retaining mechanism including:
        first and second retention members, the first and second retention members pivotable between:
            a locked position in which the first and second retention members are positioned to be received within respective first and second openings in a trocar housing of the trocar assembly when the trocar assembly is received within the distal portion of the elongate body; and
            a release position in which the first and second retention members are positioned to be spaced from the respective first and second openings in the trocar housing when the trocar assembly is received within the distal portion of the elongate body, wherein engagement of the first and second retention members with the seal member when in the locked position frictionally retains the first and second retention members in the locked position.

2. The adapter assembly of claim 1, wherein the seal member is formed of an elastomeric material.

3. The adapter assembly of claim 1, wherein the retaining mechanism includes a housing, the first and second retention members being pivotally secured to the housing.

4. The adapter assembly of claim 1, wherein the housing defines a longitudinal passage for receipt of the trocar assembly.

5. The adapter assembly of claim 4, wherein the housing further defines first and second recesses for receiving the respective first and second retention members.

6. The adapter assembly of claim 1, wherein each of the first and second retention members includes a camming surface configured to engage the trocar housing during receipt of the trocar assembly within the distal portion of the elongate body.

7. The adapter assembly of claim 1, wherein each of the first and second retention members includes a locking surface configured to engage the trocar housing when the first and second retention members are in the locked position.

8. The adapter assembly of claim 1, wherein each of the first and second retention members includes an engagement surface configured to frictionally engage the seal member to maintain the first and second retention members in the locked position.

9. The adapter assembly of claim 1, wherein each of the first and second retention members defines a slot configured to facilitate engagement of the first and second retention members by a user.

10. The adapter assembly of claim 1, further including a trocar assembly releasably securable within the distal portion of the elongate body, the trocar assembly including a trocar housing defining first and second openings.

11. A surgical stapling device comprising:
    an actuation assembly;
    an adapter assembly including an elongate body having a proximal portion and a distal portion, the proximal portion in operable engagement with the actuation assembly;
    a trocar assembly releasably securable within the distal portion of the adapter assembly, the trocar assembly including a trocar housing defining first and second openings; a seal member disposed within the distal portion of the elongate body; and
    a retaining mechanism disposed adjacent the seal member and configured to releasably secure the trocar assembly within the distal portion of the elongate body, the retaining mechanism including:
        first and second retention members, the first and second retention members pivotable between:
            a locked position in which the first and second retention members are positioned to be received within respective first and second openings in a trocar housing of the trocar assembly when the trocar assembly is received within the distal portion of the elongate body; and a release position in which the first and second retention members are positioned to be spaced from the respective first and second openings in the trocar housing when the trocar assembly is received within the distal portion of the elongate body, wherein engagement of the first and second retention members with the seal member when in the locked position frictionally retains the first and second retention members in the locked position.

12. The surgical stapling device of claim 11, wherein the seal member is formed of an elastomeric material.

13. The surgical stapling device of claim 1, wherein the retaining mechanism includes a housing, the first and second retention members being pivotally secured to the housing.

14. The surgical stapling device of claim 11, wherein the housing defines a longitudinal passage for receipt of the trocar assembly.

15. The surgical stapling device of claim 14, wherein the housing further defines first and second recesses for receiving the respective first and second retention members.

16. The surgical stapling device of claim 11, wherein each of the first and second retention members includes a camming surface configured to engage the trocar housing during receipt of the trocar assembly within the distal portion of the elongate body.

17. The surgical stapling device of claim 11, wherein each of the first and second retention members includes a locking surface configured to engage the trocar housing when the first and second retention members are in the locked position.

18. The surgical stapling device of claim 1, wherein each of the first and second retention members includes an engagement surface configured to frictionally engage the seal member to maintain the first and second retention members in the locked position.

19. The surgical stapling device of claim 11, wherein each of the first and second retention members defines a slot configured to facilitate engagement of the first and second retention members by a user.

* * * * *